United States Patent
Allen et al.

(10) Patent No.: US 7,189,531 B2
(45) Date of Patent: Mar. 13, 2007

(54) NUCLEIC ACID ENCODING PLANT SUGAR TRANSPORT PROTEINS

(75) Inventors: Stephen M. Allen, Wilmington, DE (US); William D. Hitz, Wilmington, DE (US); Anthony J. Kinney, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 453 days.

(21) Appl. No.: 10/051,902

(22) Filed: Jan. 17, 2002

(65) Prior Publication Data

US 2002/0178468 A1 Nov. 28, 2002

Related U.S. Application Data

(62) Division of application No. 09/291,922, filed on Apr. 14, 1999, now Pat. No. 6,383,776.
(60) Provisional application No. 60/083,044, filed on Apr. 24, 1998.

(51) Int. Cl.
*C12P 21/06* (2006.01)

(52) U.S. Cl. .......... 435/69.1; 435/69.1; 435/6; 435/320.1; 435/325; 435/252.3; 435/7.1; 536/23.1; 536/23.5; 530/350

(58) Field of Classification Search ........ 435/69.1, 435/6, 325, 320.1, 252.3, 7.1; 536/23.1, 23.5; 530/350
See application file for complete search history.

(56) References Cited

OTHER PUBLICATIONS

NCBI Accession No. 1778093.*
NCBI Accession No. 3080420.*
Plant Physiol., 113, pp. 663–665, 1997.*
Wells, Biochemistry, vol. 29, pp. 8509–8517, 1990.*
Seffernick et al., J. Bacteriology, vol. 183, pp. 2405–2410, 2001.*
Kull et al., J. Genet, And Breed, vol. 49, No. 1, pp. 69–76, 1995.*
Kossmann et al., Progress in Biotechnology, vol. 10, pp. 271–278, 1995.*
Jeffrey K. Griffith, Membrane transport proteins: Implications of sequence comparison, Current Opinion in Cell Biology, vol. 4:684–695, 1992.
Nathalie Noiraud, Identification of a Mannitol Transporter. AgMaT1, in Celery Phloem, The Plant Cell, vol. 13:695–705, Mar. 2001.
Tzyy–Jen Chiou et al, Isolation and Molecular Characteristics of Two Pulative Sugar Transporters from Sugar Beet (Accession No. U64902 and U64905), Plant Physiol., vol. 113. 663, Plant Gene Register PGR97–017.

* cited by examiner

*Primary Examiner*—Hope Robinson

(57) ABSTRACT

This invention relates to an isolated nucleic acid fragment encoding a sugar transport protein. The invention also relates to the construction of a chimeric gene encoding all or a portion of the sugar transport protein, in sense or antisense orientation, wherein expression of the chimeric gene results in production of altered levels of the sugar transport protein in a transformed host cell.

7 Claims, 9 Drawing Sheets

```
SEQ ID NO:29 (gi 3080420)   1  MSGAVLVAIAAAVGNLLLQGWDNATIAGAVLYIKKEFNLESNPSVEGLIVAMSLIGATLIT   60
SEQ ID NO:2                    MGGAVMVAIAAASIGNLLLQGWDNATIAGAVLYIKKEFNLQSEPLIEGLIVAMFLIGATVIT
SEQ ID NO:4                    MAGAVLVAIAAASIGNLLLQGWDNATIAGAVLYIKKEFNLHSDPLIEGLIVAM---------
SEQ ID NO:6                    MKGAVLVAIAASIGNFLQGWDNATIAGANGYIKKDLALGTT--MERIVVGMSLIGATVIT
SEQ ID NO:8                    -----------------------------------------------------------
SEQ ID NO:10                   MSGAALVAIAASIGNLLLQGWDNATIAGAVLYIKKEFQLENNPTVEGLIVA----------
SEQ ID NO:12                   -----------------------------------------------------------
SEQ ID NO:14                   -----------------------------------------------------------
SEQ ID NO:16                   -----------------------------------------------------------

SEQ ID NO:29 (gi 3080420)  61  TCsggvadwlgrrpmlilsSILYFVGSLVMIWSPNVYVLLLGRLldgfgvglvvtlvpiy   120
SEQ ID NO:2                    TSpgpradcvgrrpmlvasAVLYFVSGLVMLWAPIVYILLLARLldgfgiglavtlvply
SEQ ID NO:4                    -----------------------------------------------------------
SEQ ID NO:6                    tcsgpladwlgrrpmmiissvlyflgglvmlwspnvyvlclarlldgfgiglavtlvpvy
SEQ ID NO:8                    -----------------------------------------------------------
SEQ ID NO:10                   -----------------------------------------------------------
SEQ ID NO:12                   -----------------------------------------------------------
SEQ ID NO:14                   -----------------------------------------------------------
SEQ ID NO:16                   -----------------------------------------------------------

SEQ ID NO:29 (gi 3080420)  121 isetapp-eirGLLNTLPQFTG-SGGMFLSYCMVFGMSLMPSPSWRLMLGVLFIPSLVFF   180
SEQ ID NO:2                    isetaphrxswGXXNTLPQFIGVXGGMFLSYCMVFGMSLMPKPDWRLMLGVLSIPSLXYE
SEQ ID NO:4                    --------S---LI-------GAT-----------------------------------I-
SEQ ID NO:6                    isetaps-eirGSLNTLPQFSG-SGGMFLSYCMVFGMSLSPAPSWRLMLGVLSIPSLLYE
SEQ ID NO:8                    -----------------------------------------------------------
SEQ ID NO:10                   -----------------------------------------------------------
SEQ ID NO:12                   -----------------------------------------------------------
SEQ ID NO:14                   -----------------------------------------------------------
SEQ ID NO:16                   -----------------------------------------------------------
```

FIG. 1A

```
                                                                              240
SEQ ID NO:29 (gi 3080420)  181 FLTVFFLPESPRWLVSKGRMLEAKRVLQRLRGREDVSGEMALLVEGLGIGGETTIEEYII
SEQ ID NO:2                    GLTVFYLPESPRWLVSKGRMLEAKRVXQRLRGREDVSXEXALLVEGLGVGKDTRIXEYII
SEQ ID NO:4                    ---------------------IT-------TXS---------------------------
SEQ ID NO:6                    ------------------------------------------------------------
SEQ ID NO:8                    ALTIFFLPESPRWLVSKGRMLEAKKVLQRLRGREDVSGEMALLVEGLGIGGDTSIEEYII
SEQ ID NO:10                   ------------------------------------------------------------
SEQ ID NO:12                   ------------------------------------------------------------
SEQ ID NO:14                   ------------------------------------------------------------
SEQ ID NO:16                   ------------------------------------------------------------

300
SEQ ID NO:29 (gi 3080420)  241 GPADEVTDDHDIAVDKD-QIKLYGAEEGLSWVARPVKG----GSTMSVLSRHGSTMSRRQ
SEQ ID NO:2                    GPATEAADDLVTDGDKE-QITLYGPEEGQSWIARPSKGPIMLGSVLSLASRHGS-MVNQS
SEQ ID NO:4                    ------------------------------------------------------------
SEQ ID NO:6                    ------------------------------------------------------------
SEQ ID NO:8                    GPADDVADGHEHATEKD-KIRLYGSQAGLSWLSKPVTGQ----SSIGLASHHGS-IINQS
SEQ ID NO:10                   ------------------DPSREKD-QIKLYGPEQGQSWVARPVAGP----NSVGLVSRKGS-MANPS
SEQ ID NO:12                   ----------------S-------------------------------------------
SEQ ID NO:14                   ------------------------------------------------------------
SEQ ID NO:16                   ------------------------------------------------------------

360
SEQ ID NO:29 (gi 3080420)  301 GSLIDPLVTLFGSIHEKLPETGARGSMRSTLFPNEGSMFSVGGN--QPRHEDWD---EEN
SEQ ID NO:2                    VPLMDPIVTLFGSVHENMPQAG--GSMRSTLFPNFGSMFSVTDQ--HAKNEQWD---EEN
SEQ ID NO:4                    ------------------------------------------------------------
SEQ ID NO:6                    ------------------------------------------------------------
SEQ ID NO:8                    MPLMDPLVTLFGSIHEKLPETGARGSMRSTLFPNEGSMFSTAE--PHAKIEQWD---EES
SEQ ID NO:10                   -SLVDPLVTLFGSVHEKLPETG------STLFPHFGSMFSVGG--NQPRNEDWD---EES
SEQ ID NO:12                   ------------------------------------------WK---E-----------
SEQ ID NO:14                   ------------------------------------------------------------
SEQ ID NO:16                   ------------------------------------------------------------
```

FIG. 1B

```
                                                                        420
SEQ ID NO:29 (gi 3080420)  LVGEGEDYPSD----HGDDSEDDLHSPLISRQTTSME-KDMPHTAH--GTLSTFRHGSQV
SEQ ID NO:2                LHRDDEEYASD----GAGGDYEDNLHSPLLSRQTTSLE-KDLPPPSHGSMRRHSSL
SEQ ID NO:4                ------------------------------------------------------------
SEQ ID NO:6                LQREREDYMSDATRG----DSDDNLHSPLISRQTTSLE-KDLPPPSHGSTLGSMRRHSSL
SEQ ID NO:8                LAREGDDYVSDA--G----DSDDNLQSPLISRQTTSLD-KDIPPHAH--SNLASMRQGSLL
SEQ ID NO:10               ------------------------------------------------------------
SEQ ID NO:12               ------------------------------------------------------------
SEQ ID NO:14               ------------------------------------------------------------
SEQ ID NO:16               ------------------------------------------------------------

480
SEQ ID NO:29 (gi 3080420)  QGAQGEGAGSMGIGGGWQVAWKWTEREDESGQKEEGF--------PGSRRGSIVSLPG
SEQ ID NO:2                LGEGGDGVSSTDIGGGWQLAWKWSEKEGENGRKEGGFKRVYLHQEGVPGSRRGSIVSLPG
SEQ ID NO:4                ------------------------------------------------------------
SEQ ID NO:6                MQGSGEQGGSTGIGGGWQLAWKWTDK-GEDGKQQGGFKRIYLHEEGVSASRRGSIVSIPG
SEQ ID NO:8                HGNSGEPTGSTGIGGGWQLAWKWSEREGPDGKKEGGFKRIYLHQDGGGSGSRRGSVVSLPG
SEQ ID NO:10               ---GGEAVSSTGIGGGWQLAWKWSERQGEDGKKEGGFKRIYLHQEGVADSRRGSVVSLPG
SEQ ID NO:12               ------------------------------------------------------------
SEQ ID NO:14               ------------------------------------------------------------
SEQ ID NO:16               ------------------------------------------------------------

540
SEQ ID NO:29 (gi 3080420)  GDGTGEA--DFVQASALVSQPALYSKDLLKEHT-IGPAMVHPSE-TTKGSIWHDLHDPGV
SEQ ID NO:2                GGDVLEGS-EFVHAAALVSQSALFSKGLAEPRM-SDAAMVHPSEVAAKGSRWKDLFEPGV
SEQ ID NO:4                EG-------EFVQAAALVSQPALYSKELIDGH-PVGPAMVHPSETASKGPSWKALLEPGV
SEQ ID NO:6                GDLPTD---SEVVQAAALVSQPALYNEDLMRQR-PVGPAMIHPSETIAKGPSWSDLFEPGV
SEQ ID NO:8                GGDATQGGSGFIHAAALVSHSALYSKDLMEERMAAGPAMIHPLEAAPKGSIWKDLFEPGV
SEQ ID NO:10               ------------------------------------------------------EPGV
SEQ ID NO:12               ------------------------------------------------------------
SEQ ID NO:14               ------------------------------------------------------------
SEQ ID NO:16               ------------------------------------------------------------
```

FIG. 1C

```
                          600
SEQ ID NO:29 (gi 3080420)  KRALVVGVGLQILQQFSGINGVLYYTPQILEQAGVGILLSNMGISSSSASLLISALTTFV
SEQ ID NO:2                RRALLVGVGIQILQQFAGINGVLYYTPQILEQAGVAVILSKFGLSSASASILISSLTTLL
SEQ ID NO:4                -------------------------------------------------------VL-
SEQ ID NO:6                KHALVVGVGIQILQQFSGINGVLYYTPQILEEAGVEVLLSDIGIGSESASFLISAFTFL
SEQ ID NO:8                KHALIVGVGIQILQQFSGINGVLYYTPQILEQAGVGYLLSSLGLGSTSSSFLISAVTTLL
SEQ ID NO:10               RRALFVGVGIQMLQQFAGINGVLYYTPQILEQAGVAVLLSNLGLSSASASILISSLTTLL
SEQ ID NO:12               KHALFVGIGLQILQQFAGINGVLYYTPQILEQAGVGVLLSNIGLSSSSASILISALTTLL

660
SEQ ID NO:29 (gi 3080420)  MLPAIAVAMRLMDLSGRRTLLLTTIPILIASLLIVIVISNLVHMNSIVHAVLSTVSVVLYF
SEQ ID NO:2                MLPCIGFAMLLMDLSGRRFLLLGTIPILIASLVILIVVSNLIDLGTLAHALLSTISVIYF
SEQ ID NO:4                ------------------TLILVNILDVGTMVHASLSTVSVILYF
SEQ ID NO:6                MLPCIGVAMKLMDVSGRRQLLLTTIPVLIVSLIIIVIGSLVNFGNVAHAAISTVCVVVYF
SEQ ID NO:8                MLPCIAIAMRLMDISGRRTLLLSTIPVLIAALLIVLGSLVDLGSTANASISTISVIVYF
SEQ ID NO:10               MLPSIGVAMRLMDISGRRFLLLGTIPILIASLIVLGVVNVINLSTVPHAVLSTVSVIVYF
SEQ ID NO:12               MLPSIGIAMRLMDMSGRRFLLLSTIPVLIVALAVLVLVNVLDVGTMVHAALSTISVIVYF

720
SEQ ID NO:29 (gi 3080420)  CFFVMGFGPAPNILCSEIFPTRVRGICIAICALTFWICDIIVTYSLPVLLKSIGLAGVFG
SEQ ID NO:2                CCFVMGFGPIPNILCAEIFPTRVRGLCIAICALTFWIGDIIVTYSLPVMLNAIGLAGVFS
SEQ ID NO:4                CFFVMGFGPIPNILCAEIFPTTVRGLCIAICALVFWIGDIIITYSLPVMLGSLGLGGVFA
SEQ ID NO:6                CCFVMGFGPYGPIPNILCAEIFPTRVRGLCIAICALVFWIGDIIVTYSLPVMLGSLGLGVFA
SEQ ID NO:8                CCFVMGFGPIPNILCAEIFPTRVRGLCIAICALTFWICDIIVTYTLPVMLNSVGLAGVFG
SEQ ID NO:10               CCFVMGFGPIPNILCAEIFPTRVRGVCIAICALTFWICDIIVTYSLPVMLNAIGLAGVFG
SEQ ID NO:12               CCFVMGFGPIPNILCAEIFPTSVRGICIAICALTFWIGDIIVTYTLPVMLNAIGLAGVFG
```

FIG. 1D

```
                          721                                                            767
SEQ ID NO:29 (gi 3080420) MYAIVCCISWFVFVFIKVPETKGMPLEVITEFFSVGARQAEAA----KNE
SEQ ID NO:2               IYAVVCLISFVFVFLKVPETKGMPLEVITEFFAVGAKQAAA------KA
SEQ ID NO:4               ------------------------------------------------
SEQ ID NO:6               IYAVVCILAFLFVEMKVPETKGMPLEVITEFFSVGAKQ-AKE----D
SEQ ID NO:8               IYAVVCFISWIFVFLKVPETKGMPLEVISEFFSVGAKQAASA---KNE
SEQ ID NO:10              IYAVVCFIAWVFVFLKVPETKGMPLEVIIEFFSVGAKQFDDA--KHN
SEQ ID NO:12              ------------------------------------------------
SEQ ID NO:14              IYAVVCCIAFVFVYLKVPETKGMPLEVITEFFAVGAKQ-AQA--TIA
SEQ ID NO:16              IYAIVCVLAFVFVYMKVPETKGMPLEVITEFFSVGAKQ-GKE--ATD
```

FIG. 1E

```
                1                                                            60
SEQ ID NO:30    MSEG------------TNKAMSDPPPTTASKVIA---DF-DPLKKPPKRN----KFAFACAT
SEQ ID NO:18    SR-----------------------AQSEPSTMASA---PL--PAAIEPGKKGNVKFAFACXI
SEQ ID NO:20    M-----------------------------------ASD--ELAK--AVEPRKKGNVKYASICAI
SEQ ID NO:22    ------------------------------------MASA--AL--PEAVAPKKKGNVRFAFACAI
SEQ ID NO:24    MTEG-------------------KIVEAAEAH----KTLQ--DF-DPPKKR-KRN----KYAFACAM
SEQ ID NO:26    ------------------------------------MDRA--AL--PAAVEPKKKGNVRFAFACAI
SEQ ID NO:28    MKMS-------------------PERKGAEDKEEGSRMASA---ALPEPGAVHPRNKGNFKYAFTCAL 61                                                           120
SEQ ID NO:30    LASMTSVLLGY---------------------DIGVMSGAIIYLKEDWHISDTQIGVLVG
SEQ ID NO:18    LASMTSILLGY---------------------DIGVMSGASLYIKKDLKISDVKLEILMG
SEQ ID NO:20    LASMASVILGY---------------------DIGVMSGAAMYIKKDLNITDVQLEILIG
SEQ ID NO:22    LASMTSILLGY---------------------DIGVMSGASLYIKKDFNISDGKVEVLMG
SEQ ID NO:24    LASMTSILLGY---------------------DIGVMSGAAIYIKRDLKVSDEQIEILLG
SEQ ID NO:26    LASMTSILLGY---------------------DIGVMSGASLYIQKDLKINDTQLEVLMG
SEQ ID NO:28    CASMATIVLGY---------------------DVGVMSGASLYIKRDLQITDVQLEIMMG 121                                                          180
SEQ ID NO:30    ILNIYCLFGSFAAGRTSDWIGRRYTIVLAGAIFEVGALLMGFATNYAFLMVGRFVTGIGV
SEQ ID NO:18    ILNVYSLIGSXAAGRTSDWIGRRXTIVFAAVIFFAGAXLMGFAVNYWMLMFGRFVAGIGV
SEQ ID NO:20    ILSLYSLFGSFAGARTSDRIGRRLTVVFAAVIFVGSLLMGFAVNYGMLMAGRFVAGVGV
SEQ ID NO:22    ILNLYSLIGSFAAGRTSDWIGRRYTIVFAAVIFEAGXFLMGFAVNYAMLMFGRFVAGIGV
SEQ ID NO:24    IINLYSLIGSCIAGRTSDWIGPRYTIVFAGTIFFVGALLMGFSPNYSFLMFGRFVAGIGI
SEQ ID NO:26    ILNVYSLIGSFAAGRTSDWIGRRFTIVFAAVIFEAGALIMGFSVNYAMLMFGRFVAGIGV
SEQ ID NO:28    ILSVYALIGSFLGARTSDWVGRRVTVVFAAAIFNNGSLLMGFAVNYAMLMGFAVNYAMLMVGRFVTGIGV
```

FIG. 2A

```
          181                                                            240
SEQ ID NO:30   GYALMIAPVYTAEVSPASSRGFLTSFPEVFINAGILLGYISNLAFSSLPTHLSWREMLGI
SEQ ID NO:18   GYALMIATVYTAEVSPXSPAASRGFLTSFPEVFI---------------------------
SEQ ID NO:20   GYGGMIAPVYTAEISPAASRGFLTTFPEVFINIGILLGYLSNFAFARLPLHLGWRVMLAI
SEQ ID NO:22   GYALMIAPVYTAEVSPASARGFLTSFPEVFINFGILLGYVSNYAFSRLPLNLGWRIMLGI
SEQ ID NO:24   GYALMIAPVYTAEVSPASSRGFLTSFPEVFINGGILLGYILGYISNYAFSKLTLKVGWRMMLGV
SEQ ID NO:26   GYALMIAPVNTGEVSPASARGVLTSFPEVFINFGILLGYVSNFAFARLSLRLGWRIMLGI
SEQ ID NO:28   GYAIMVAPVYTPEVSPASARGFLTSFTEVFINVGILLGYVSNYAFARLPLHLSWRVMLGI 241                                                            300
SEQ ID NO:30   GAIPSIFLAIGVLAMPESPRWLVMQGRLGDAKKVLNRISDSPEEAQLRLSEIKQTAGIPA
SEQ ID NO:18   ------------------------------------------------------------
SEQ ID NO:20   GAVPSGLLALLIVFCMPESPRWLVLKGRLADARAVLEKTSATPEEAAERLADIKAAAGIPK
SEQ ID NO:22   GAAPSVLLALMVLGMPESPRWLVMKGRLADAKVVLEKTVLEKTSDTAEEAAERLADIKAAAGIPE
SEQ ID NO:24   GAIPSVLLTVGVLAMPESPRWLVMRGRLGEARKVLNKTSDSKEEAQLRLAEIKQAAGIPE
SEQ ID NO:26   GAVPSVLLAFMVLGMPESPRWLVMKGRLADAKVVLAKTSDTPEEAAERIADIKTAAGIPL
SEQ ID NO:28   GAVPSALLALMVFGMPESPRWLVMKGRLADARAVLAKTSDTPEEAVERLDQIKAAAGIPR 301                                                            360
SEQ ID NO:30   ECDEDIYKVEKTKIKSGNA-VWKELFFNPTPAVRRAVIAGIGIHFFQQASGIDAVVLYSP
SEQ ID NO:18   ------------------------------------------------------------
SEQ ID NO:20   GLDGDVVTVPGKEQGGGELQWKKLIILSPTPAVRRILLSAVGLHFFQQASGSDSVVQYSA
SEQ ID NO:22   ELDGDVVTVPK-RGSGNEKRVWKELILSPTPAMRRILSGIGIHFFQHALGIHSVVFYSP
SEQ ID NO:24   SCNDDVVQNKQS--NGEG-VWKELFLYPTPAIRHIVIAALGIHFFQQASGVDAVVLYSP
SEQ ID NO:26   GLDGDVVPVPKNKGSSEEKRVLKDLILSPTIAMRHILIAGIHFFQQSSGIDAVVLYSP
SEQ ID NO:28   ELDGDVVVMP-KTKGGQEKQVWKELIFSPTPAMRRILLAALGIHFFQQATGSDSVVLYSP
```

FIG. 2B

```
                                                                      420
361   RIFQSAGITNARKQLLATVAVGVVKTLFLFILVATFQLDKYGRRPLLLTSVGGMIIAILTLA
SEQ ID NO:30
SEQ ID NO:18   ------------------------------------------------------------
SEQ ID NO:20   RLFKSAGITDDNKLLGVTCAVGVVTKTFFILVATFLLDRAGRRPLLLISTGGMIVSLICLG
SEQ ID NO:22   LVFKSPGLTNDKHFLGTTWPFGVTKRLFILLATFFIDGVGRRPLLLGSTGGIILSLIGLG
SEQ ID NO:24   RIFEKAGITNDTHKLLATVAVGFVKTVFILAATFTLDRVGRRPLLLSSVGGMVLSLLTLA
SEQ ID NO:26   LVFKSAGITGDSRLRGTTVAVGATNTVFILVATFLLDRIRRRPLIVLTSTGGMIVSLVGLA
SEQ ID NO:28   RVFQSAGITGDNHLLGATCAMGVMKTLFILVATFQLDRVGRRPLLLTSTAGMLACLIGLG 480
421   MSLTVID-HSHHKITWAIALCITMVCAVVASFSIGLGPITWVYSSEVFPLRLRAQGTSMG
SEQ ID NO:30
SEQ ID NO:18   ------------------------------------------------------------
SEQ ID NO:20   SGLTVAGHHPDTKVAWAVALCIASTLSYIAFFSIGLGPITGVYTSEIFPLQVRALGFAVG
SEQ ID NO:22   AGLTVVGQHPDAKIPWAIGLSIASTLAYVAFFSIGLGPITWVYSSEIFPLQVRALGCSLG
SEQ ID NO:24   ISLTVID-HSERKLMWAVGSSIAMVLAYVATFSIGAGPITWVYSSEIFPLRLRAQGAAAG
SEQ ID NO:26   TGLTVISRHPDEKITWAIVLCIFCIMAYVAFFSIGLGPITWVYSSEIFPLHVRALGCSLG
SEQ ID NO:28   TGLTVVGRHPDAKVPWAIGLCIVSILAYVSFFSIGLGPLTSVYTSEVFPLRVRALGFALG 540
481   VAVNRVVSGVISIFFLPLSHKITTGGAFFLFGGIAIIAWFFFLTFLPETRGRTLENMHEL
SEQ ID NO:30
SEQ ID NO:18   ------------------------------------------------------------
SEQ ID NO:20   VASNRVTSAVISMTFLSLSKAITIGGSFFLYSGIAAVAWVFFFTCLPETRGRTLEEMGKL
SEQ ID NO:22   VAANRVTSGVISMTFLSLSKAITIGGSFFLYSGIAALAWVFFYTYLPETRGRTLEEMSKL
SEQ ID NO:24   VAVNRTTSAVVSMTFLSLITRAITIGGAFFLYCGIATVGWIFFYTVLPETRGKTLEDMEGS
SEQ ID NO:26   VAVNRLTSGVISMTFISLSKAMTIGGAFFLFAGIASFAWVFFFAYLPETRGRTLEDMSSL
SEQ ID NO:28   TSCNRVTSAAVSMSFLSLSKAITIGGSFFLYAGIAAIGWIFFTFIPETRGLPLEEIGKL
```

FIG. 2C

```
             541                                                       590
SEQ ID NO:30 FEDFRWRESFPGNKSNNDENSTRKQSNGNDKSQVQLGETTTSTTVTNDNH
SEQ ID NO:18 ----------------------------------------------TS----
SEQ ID NO:20 FGM-------------PDTGMAEEAEDA-AAKEKVVELPSSK--------
SEQ ID NO:22 FGD-------------TAAASESDEPAKEK---KKVEMAATN--------
SEQ ID NO:24 FGTFRSKSN---ASKAVENENG-------QVAQVQLG-------TNVQT-
SEQ ID NO:26 FGN-------------TATHKQGAAEADDDAGEKKVEMAATN--------
SEQ ID NO:28 FGM-------------TDTAVEAQDTAT-KDKAKVGEM----N-------
```

FIG. 2D

NUCLEIC ACID ENCODING PLANT SUGAR TRANSPORT PROTEINS

This application is a divisional of U.S. application Ser. No. 09/291,922, filed Apr. 14, 1999, now granted as U.S. Pat. No. 6,383,776, whose contents are incorporated by reference, and claims the benefit of U.S. Provisional Application No. 60/083,044, filed Apr. 24, 1998.

FIELD OF THE INVENTION

This invention is in the field of plant molecular biology. More specifically, this invention pertains to nucleic acid fragments encoding sugar transport proteins in plants and seeds.

BACKGROUND OF THE INVENTION

Sugar is one form of carbohydrate produced in photosynthesizing cells in most higher plants and is the main form of transported carbon in most annual field crops such as corn, rice, soybeans and wheat. As such its movement and concentration across various plant membranes is critical to plant growth and development. In addition sugar is the main form of carbon that moves into developing seeds of soybeans, rice, corn and wheat. This movement and concentration is accomplished by the action of carrier proteins that act to transport sugar against a concentration gradient often by coupling sugar movement to the opposite vectoral movement of a proton. Specific sugar carrier proteins from these crop plants could be manipulated in efforts to control carbon flux and the timing and extent of sugar transport phenomena (e.g., grain fill duration) that are important factors in crop yield and quality. Accordingly, the availability of nucleic acid sequences encoding all or a portion of sugar transport proteins would facilitate dies to better understand carbon flux and sugar transport in plants, provide genetic tools for the manipulation of sugar transport, and provide a means to control carbohydrate transport and distribution in plant cells.

SUMMARY OF THE INVENTION

The instant invention relates to isolated nucleic acid fragments encoding sugar transport proteins. Specifically, this invention concerns an isolated nucleic acid fragment encoding an *Arabidopsis thaliana*-like sugar transport protein or *Beta vulgaris*-like sugar transport protein. In addition, this invention relates to a nucleic acid fragment that is complementary to the nucleic acid fragment encoding an *Arabidopsis thaliana*-like sugar transport protein or *Beta vulgaris*-like sugar transport protein.

An additional embodiment of the instant invention pertains to a polypeptide encoding all or a substantial portion of a sugar transport protein selected from the group consisting of *Arabidopsis thaliana*-like sugar transport protein and *Beta vulgaris*-like sugar transport protein.

In another embodiment, the instant invention relates to a chimeric gene encoding an *Arabidopsis thaliana*-like sugar transport protein or *Beta vulgaris*-like sugar transport protein, or to a chimeric gene that comprises a nucleic acid fragment that is complementary to a nucleic acid fragment encoding an *Arabidopsis thaliana*-like sugar transport protein or *Beta vulgaris*-like sugar transport protein, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding an *Arabidopsis thaliana*-like sugar transport protein or *Beta vulgaris*-like sugar transport protein, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of an *Arabidopsis thaliana*-like sugar transport protein or *Beta vulgaris*-like sugar transport protein in a transformed host cell comprising: a) transforming a host cell with a chimeric gene comprising a nucleic acid fragment encoding an *Arabidopsis thaliana*-like sugar transport protein or *Beta vulgaris*-like sugar transport protein; and b) growing the transformed host cell under conditions that are suitable for expression of the chimeric gene wherein expression of the chimeric gene results in production of altered levels of *Arabidopsis thaliana*-like sugar transport protein or *Beta vulgaris*-like sugar transport protein in the transformed host cell.

An addition embodiment of the instant invention concerns a method for obtaining a nucleic acid fragment encoding all or a substantial portion of an amino acid sequence encoding an *Arabidopsis thaliana*-like sugar transport protein or *Beta vulgaris*-like sugar transport protein.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIGS. 1A, 1B, 1C, 1D and 1E show a comparison of the amino acid sequences set forth in SEQ ID NOs:2, 4, 6, 8, 10, 12, 14 and 16 with the *Arabidopsis thaliana*-like sugar transport protein amino acid sequence set forth in SEQ ID NO:29. Amino acid designations in small case letters represent regions that are thought to be *Arabidopsis thaliana*-like sugar transport protein signatures.

FIGS. 2A, 2B, 2C and 2D show a comparison of the amino acid sequences set forth in SEQ ID NOs:18, 20, 22, 24, 26 and 28 with the *Beta vulgaris*-like sugar transport protein amino acid sequence set forth in SEQ ID NO:30.

The following sequence descriptions and Sequence Listing attached hereto comply with the rules governing nucleotide and/or amino acid sequence disclosures in patent applications as set forth in 37 C.F.R. §1.821-1.825.

SEQ ID NO:1 is the nucleotide sequence comprising a contig assembled from the cDNA inserts in clones p0032.crcba66r, p0097.cqran41r, cr1n.pk0143.h10, p0128.cpict38, p0106.cjlpm67r, cil1c.pk00.1.f21, p0072.comgi92r, p0114.cimm181r and p0002.cgevb73r encoding a corn *Arabidopsis thaliana*-like sugar transport protein.

SEQ ID NO:2 is the deduced amino acid sequence of an *Arabidopsis thaliana*-like sugar transport protein derived from the nucleotide sequence of SEQ ID NO:1.

SEQ ID NO:3 is the nucleotide sequence comprising a contig assembled from the cDNA inserts in clones rlr12.pk0013.d11 and rds1c.pk007.n17 encoding a portion of a rice *Arabidopsis thaliana*-like sugar transport protein.

SEQ ID NO:4 is the deduced amino acid sequence of a portion of an *Arabidopsis thaliana*-like sugar transport protein derived from the nucleotide sequence of SEQ ID NO:3.

SEQ ID NO:5 is the nucleotide sequence comprising a the entire cDNA insert in clone rls6.pk0003.d5 encoding a portion of a rice *Arabidopsis thaliana*-like sugar transport protein.

SEQ ID NO:6 is the deduced amino acid sequence of an *Arabidopsis thaliana*-like sugar transport protein derived from the nucleotide sequence of SEQ ID NO:5.

SEQ ID NO:7 is the nucleotide sequence comprising a contig assembled from the cDNA inserts in clones sgs4c.pk005.c9, sfl1.pk0079.a4 and sdp3c.pk012.i1 encoding a soybean *Arabidopsis thaliana*-like sugar transport protein.

SEQ ID NO:8 is the deduced amino acid sequence of an *Arabidopsis thaliana*-like sugar transport protein derived from the nucleotide sequence of SEQ ID NO:7.

SEQ ID NO:9 is the nucleotide sequence comprising a portion of the cDNA insert in clone ss1.pk0022.f1 encoding a portion of a soybean *Arabidopsis thaliana*-like sugar transport protein.

SEQ ID NO:10 is the deduced amino acid sequence of a portion of an *Arabidopsis thaliana*-like sugar transport protein derived from the nucleotide sequence of SEQ ID NO:9.

SEQ ID NO:11 is the nucleotide sequence comprising a portion of the cDNA insert in clone wlk8.pk0001.a12 encoding a portion of a wheat *Arabidopsis thaliana*-like sugar transport protein.

SEQ ID NO:12 is the deduced amino acid sequence of a portion of an *Arabidopsis thaliana*-like sugar transport protein derived from the nucleotide sequence of SEQ ID NO:11.

SEQ ID NO:13 is the nucleotide sequence comprising a contig assembled from the cDNA inserts in clones wlm96.pk043.e19 and wre1n.pk0062.g6 encoding a portion of a wheat *Arabidopsis thaliana*-like sugar transport protein.

SEQ ID NO:14 is the deduced amino acid sequence of a portion of an *Arabidopsis thaliana*-like sugar transport protein derived from the nucleotide sequence of SEQ ID NO:13.

SEQ ID NO:15 is the nucleotide sequence comprising a portion of the cDNA insert in clone wre1n.pk0006.b4 encoding a portion of a wheat *Arabidopsis thaliana*-like sugar transport protein.

SEQ ID NO:16 is the deduced amino acid sequence of a portion of an *Arabidopsis thaliana*-like sugar transport protein derived from the nucleotide sequence of SEQ ID NO:15.

SEQ ID NO:17 is the nucleotide sequence comprising a portion of the cDNA insert in clone cc1.mn0002.h1 encoding a portion of a corn *Beta vulgaris*-like sugar transport protein.

SEQ ID NO:18 is the deduced amino acid sequence of a portion of a *Beta vulgaris*-like sugar transport protein derived from the nucleotide sequence of SEQ ID NO:17.

SEQ ID NO:19 is the nucleotide sequence comprising the entire cDNA insert in clone cepe7.pk0018.g3 encoding a corn *Beta vulgaris*-like sugar transport protein.

SEQ ID NO:20 is the deduced amino acid sequence of a *Beta vulgaris*-like sugar transport protein derived from the nucleotide sequence of SEQ ID NO:19.

SEQ ID NO:21 is the nucleotide sequence comprising a contig assembled from the cDNA inserts in clones rlr6.pk0005.b10, rl0n.pk102.p24 and rl0n.pk107.p2 encoding a rice *Beta vulgaris*-like sugar transport protein.

SEQ ID NO:22 is the deduced amino acid sequence of a *Beta vulgaris*-like sugar transport protein derived from the nucleotide sequence of SEQ ID NO:21.

SEQ ID NO:23 is the nucleotide sequence comprising a contig assembled from the cDNA inserts in clones sr1.pk0061.g8, sfl1.pk0058.h12, sgs2c.pk004.o17 and sre.pk0032.h6 encoding a soybean *Beta vulgaris*-like sugar transport protein.

SEQ ID NO:24 is the deduced amino acid sequence of a *Beta vulgaris*-like sugar transport protein derived from the nucleotide sequence of SEQ ID NO:23.

SEQ ID NO:25 is the nucleotide sequence comprising the entire cDNA insert in clone wlk8.pk0001.a11 encoding a wheat *Beta vulgaris*-like sugar transport protein.

SEQ ID NO:26 is the deduced amino acid sequence of a *Beta vulgaris*-like sugar transport protein derived from the nucleotide sequence of SEQ ID NO:25.

SEQ ID NO:27 is the nucleotide sequence comprising the entire cDNA insert in clone wlm1.pk0012.h1 encoding a wheat *Beta vulgaris*-like sugar transport protein.

SEQ ID NO:28 is the deduced amino acid sequence of a *Beta vulgaris*-like sugar transport protein derived from the nucleotide sequence of SEQ ID NO:28.

SEQ ID NO:29 is the amino acid sequence of an *Arabidopsis thaliana* (NCBI Identification No. gi 3080420) sugar transport protein.

SEQ ID NO:30 is the amino acid sequence of a *Beta vulgaris* (NCBI Identification No. gi 1778093) sugar transport protein.

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. As used herein, "contig" refers to an assemblage of overlapping nucleic acid sequences to form one contiguous nucleotide sequence. For example, several DNA sequences can be compared and aligned to identify common or overlapping regions. The individual sequences can then be assembled into a single contiguous nucleotide sequence.

As used herein, "substantially similar" refers to nucleic acid fragments wherein changes in one or more nucleotide bases results in substitution of one or more amino acids, but do not affect the functional properties of the protein encoded by the DNA sequence.

"Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products.

Moreover, substantially similar nucleic acid fragments may also be characterized by their ability to hybridize, under stringent conditions (0.1×SSC, 0.1% SDS, 65° C.), with the nucleic acid fragments disclosed herein.

Substantially similar nucleic acid fragments of the instant invention may also be characterized by the percent similarity of the amino acid sequences that they encode to the amino acid sequences disclosed herein, as determined by algorithms commonly employed by those skilled in this art. Preferred are those nucleic acid fragments whose nucleotide sequences encode amino acid sequences that are 90% similar to the amino acid sequences reported herein. Most preferred are nucleic acid fragments that encode amino acid sequences that are 95% similar to the amino acid sequences reported herein. Sequence alignments and percent similarity calculations were performed using the Megalign program of the LASARGENE bioinformatics computing suite (DNASTAR Inc., Madison, Wis.). Multiple alignment of the sequences was performed using the Clustal method of alignment (Higgins, D. G. and Sharp, P. M. (1989) CABIOS. 5:151–153) with the default parameters (GAP PENALTY=10, GAP LENGTH PENALTY=10) (hereafter, Clustal algorithm). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the *Arabidopsis thaliana*-like sugar transport proteins or *Beta vulgaris*-like sugar transport proteins as set forth in SEQ ID NOs:2, 4, 6, 8, 10, 12, 14, 16, 18, 20, 22, 24, 26 and 28. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Maniatis").

Nucleic acid fragments encoding at least a portion of several sugar transport proteins have been isolated and identified by comparison of random plant cDNA sequences to public databases containing nucleotide and protein sequences using the BLAST algorithms well known to those skilled in the art. Table 1 lists the proteins that are described herein, and the designation of the cDNA clones that comprise the nucleic acid fragments encoding these proteins.

TABLE 1

Sugar Transport Proteins

| Enzyme | Clone | Plant |
|---|---|---|
| Sugar Transport Protein (*Arabidopsis*-like) | p0032.crcba66r | Corn |
| | p0097.cqran41r | Corn |
| | cr1n.pk0143.h10 | Corn |
| | p0128.cpict38 | Corn |
| | p0106.cjlpm67r | Corn |
| | ci11c.pk001.f21 | Corn |
| | p0072.comgi92r | Corn |
| | p0114.cimm181r | Corn |
| | p0002.cgevb73r | Corn |
| | rds1c.pk007.n17 | Rice |
| | rlr12.pk0013.d11 | Rice |
| | rls6.pk0003.d5 | Rice |
| | sgs4c.pk005.c9 | Soybean |
| | sfl1.pk0079.a4 | Soybean |
| | sdp3c.pk012.i1 | Soybean |
| | ss1.pk0022.f1 | Soybean |
| | wlk8.pk0001.a12 | Wheat |
| | wlm96.pk043.e19 | Wheat |
| | wre1n.pk0062.g6 | Wheat |
| | wre1n.pk0006.b4 | Wheat |
| Sugar Transport Protein (*Beta vulgaris*-like) | cc1.mn0002.h1 | Corn |
| | cepe7.pk0018.g3 | Corn |
| | rlr6.pk0005.b10 | Rice |
| | rl0n.pk102.p24 | Rice |
| | rl0n.pk107.p2 | Rice |
| | sr1.pk0061.g8 | Soybean |
| | sfl1.pk0058.h12 | Soybean |
| | sgs2c.pk004.o17 | Soybean |
| | sre.pk0032.h6 | Soybean |
| | wlk8.pk0001.a11 | Wheat |
| | wlm1.pk0012.h1 | Wheat |

The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other *Arabidopsis thaliana*-like sugar transport proteins or *Beta vulgaris*-like sugar transport proteins, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which the disclosed *Arabidopsis thaliana*-like sugar transport proteins or *Beta vulgaris*-like sugar transport proteins are present at higher or lower levels than normal or in cell types or developmental stages in which they are not normally found. This would have the effect of altering the level of sugar transport in those cells.

Overexpression of the *Arabidopsis thaliana*-like sugar transport proteins or *Beta vulgaris*-like sugar transport proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant sugar transport proteins to different cellular compartments, or to facilitate its secretion from the cell. It is thus envisioned that the chimeric gene described above may be further supplemented by altering the coding sequence to encode *Arabidopsis thaliana*-like sugar transport proteins or *Beta vulgaris*-like sugar transport proteins with appropriate intracellular targeting sequences such as transit sequences (Keegstra, K. (1989) *Cell* 56:247–253), signal sequences or sequences encoding endoplasmic reticulum localization (Chrispeels, J. J., (1991) *Ann. Rev. Plant Phys. Plant Mol. Biol.* 42:21–53), or nuclear localization signals (Raikhel, N. (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding *Arabidopsis thaliana*-like sugar transport proteins or *Beta vulgaris*-like sugar transport proteins in plants for some applications. In order to accomplish this, a chimeric gene designed for co-suppression of the instant sugar transport proteins can be constructed by linking a gene or gene fragment encoding an *Arabidopsis thaliana*-like sugar transport protein or *Beta vulgaris*-like sugar transport protein to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

The instant *Arabidopsis thaliana*-like sugar transport proteins or *Beta vulgaris*-like sugar transport proteins (or portions thereof) may be produced in heterologous host cells, particularly in the cells of microbial hosts, and can be used to prepare antibodies to the these proteins by methods well known to those skilled in the art. The antibodies are useful for detecting *Arabidopsis thaliana*-like sugar transport proteins or *Beta vulgaris*-like sugar transport proteins in situ in cells or in vitro in cell extracts. Preferred heterologous host cells for production of the instant sugar transport proteins are microbial hosts. Microbial expression systems and expression vectors containing regulatory sequences that direct high level expression of foreign proteins are well known to those skilled in the art. Any of these could be used to construct a chimeric gene for production of the instant *Arabidopsis thaliana*-like sugar transport proteins or *Beta vulgaris*-like sugar transport proteins. This chimeric gene could then be introduced into appropriate microorganisms via transformation to provide high level expression of the encoded sugar transport protein. An example of a vector for high level expression of the instant *Arabidopsis thaliana*-like sugar transport proteins or *Beta vulgaris*-like sugar transport proteins in a bacterial host is provided (Example 7).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al., (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am. J. Hum. Genet.* 32:314–331).

The production and use of plant gene-derived probes for use in genetic mapping is described in R. Bernatzky, R. and Tanksley, S. D. (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask, B. J. (1991) *Trends Genet.* 7:149–154). Although current methods of FISH mapping favor use of large clones (several to several hundred KB; see Laan, M. et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) *J. Lab. Clin. Med.* 114(2):95–96), polymorphism of PCR-amplified fragments (CAPS; Sheffield, V. C. et al. (1993) *Genomics* 16:325–332), allele-specific ligation (Landegren, U. et al. (1988) *Science* 241:1077–1080), nucleotide extension reactions (Sokolov, B. P. (1990) *Nucleic Acid Res.* 18:3671), Radiation Hybrid Mapping (Walter, M. A. et al. (1997) *Nature Genetics* 7:22–28) and Happy Mapping (Dear, P. H. and Cook, P. R. (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer, (1989) *Proc. Natl. Acad. Sci USA* 86:9402; Koes et al., (1995) *Proc. Natl. Acad. Sci USA* 92:8149; Bensen et al., (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the *Arabidopsis thaliana*-like sugar transport protein or *Beta vulgaris*-like sugar transport protein. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding an *Arabidopsis thaliana*-like sugar transport protein or *Beta vulgaris*-like sugar transport protein can be identified and obtained. This mutant plant can then be used to determine or confirm the natural function of the *Arabidopsis thaliana*-like sugar transport protein or *Beta vulgaris*-like sugar transport protein gene product.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries: Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| cc1 | Corn (*Zea mays* L.) callus stage 1** | cc1.mn0002.h1 |
| Cepe7 | Corn (*Zea mays* L.) epicotyl from 7 day old etiolated seedling | cepe7.pk0018.g3 |
| cil1c | Corn (*Zea mays* L.) pooled immature leaf tissue at V4, V6 and V8** | cil1c.pk001.f21 |
| cr1n | Corn (*Zea mays* L.) root from 7 day seedlings grown in light* | cr1n.pk0143.h10 |
| p0002 | Corn (*Zea mays* L.) tassel: premeiotic > early uninucleate | p0002.cgevb73r |
| p0032 | Corn (*Zea mays* L.) regenernerating callus, 10 and 14 days after auxin removal. | p0032.crcba66r |
| p00072 | Corn (*Zea mays* L.) 14 days after planting etiolated seedling: mesocotyl | p0072.comgi92r |
| p0097 | Corn (*Zea mays* L.) V9, 7 cm whorl section after application of European Corn Borer | p0097.cqran41r |
| p0106 | Corn (*Zea mays* L.) 5 days after pollenation whole kernels* | p0106.cjlpm67r |
| p0114 | Corn (*Zea mays* L.) intercalary meristem of expanding internodes 5–9 at V10 stage* | p0114.cimm181r |
| p0128 | Corn (*Zea mays* L.) pooled primary and secondary immature ear | p0128.cpict38 |
| Rds1c | Rice (*Oryza sativa*, YM) developing seeds | rds1c.pk007.n17 |
| rlr6 | Rice (*Oryza sativa* L.) leaf (15 days after germination) 6 hrs after infection of *Magaporthe grisea* strain 4360-R-62 (AVR2-YAMO); Resistant | rlr6.pk0005.b10 |
| rl0n | Rice (*Oryza sativa* L.) 15 day leaf* | rl0n.pk102.p24 rl0n.pk107.p2 |
| rlr12 | Rice (*Oryza sativa* L.) leaf, 15 days after germination, 12 hours after infection of *Magaporthe grisea* strain 4360-R-62 (AVR2-YAMO); Resistant | rlr12.pk0013.d11 |
| rls6 | Rice (*Oryza sativa* L.) leaf, 15 days after germination, 6 hrs after infection of *Magaporthe grisea* strain 4360-R-67 (avr2-yamo); Susceptible | rls6.pk0003.d5 |

TABLE 2-continued cDNA Libraries from Corn, Rice, Soybean and Wheat

| Library | Tissue | Clone |
| --- | --- | --- |
| sdp3c | Soybean (*Glycine max* L.) developing pods 8–9 mm | sdp3c.pk012.i1 |
| sfl1 | Soybean (*Glycine max* L.) immature flower | sfl1.pk0079.a4 |
| | | sfl1.pk0058.h12 |
| sgs2c | Soybean (*Glycine max* L.) seeds 14 hrs after germination | sgs2c.pk004.o17 |
| sgs4c | Soybean (*Glycine max* L.) seeds 2 days after germination | sgs4c.pk005.c9 |
| sr1 | Soybean (*Glycine max* L.) root library | sr1.pk0061.g8 |
| sre | Soybean (*Glycine max* L.) root elongation | sre.pk0032.h6 |
| ss1 | Soybean (*Glycine max* L.) seedling 5–10 day | ss1.pk0022.f1 |
| wlk8 | Wheat (*Triticum aestivum* L.) seedlings 8 hr after treatment with fungicide\*\*\* | wlk8.pk0001.a11 |
| | | wlk8.pk0001.a12 |
| wlm1 | Wheat (*Triticum aestivum* L.) seedlings 1 hr after inoculation with *Erysiphe graminis* f. sp *tritici* | wlm1.pk0012.h1 |
| wlm96 | Wheat (*Triticum aestivum* L.) seedlings 96 hr after inoculation w/*E. graminis* | wlm96.pk043.e19 |
| wre1n | Wheat (*Triticum aestivum* L.) root; 7 day old etiolated seedling\* | wre1n.pk0006.b4 |
| | | wre1n.pk0062.g6 |

\*These libraries were normalized essentially as described in U.S. Pat. No. 5,482,845
\*\*V4, V6 and V8 refer to stages of corn growth. The descriptions can be found in "How a Corn Plant Develops" Special Report No. 48, Iowa State University of Science and Technology Cooperative Extension Service Ames, Iowa, Reprinted February 1996.
\*\*\*Application of 6-iodo-2-propoxy-3-propyl-4(3H)-quinazolinone; synthesis and methods of using this compound are described in USSN 08/545,827, incorporated herein by reference.

cDNA libraries were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs" ; see Adams, M. D. et al., (1991) *Science* 252:1651). The resulting ESTs were analyzed using a Perkin Elmer Model 377 fluorescent sequencer.

Example 2

Identification of cDNA Clones

ESTs encoding sugar transport proteins were identified by conducting BLAST (Basic Local Alignment Search Tool; Altschul, S. F., et al., (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272 and Altschul, Stephen F., et al. (1997) *Nucleic Acids Res.* 25:3389–3402) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding *Arabidopsis thaliana*-Like Sugar Transport Proteins The BLASTX search using the EST sequences from several corn, rice, soybean and wheat clones revealed similarity of the proteins encoded by the cDNAs to a sugar transport protein from *Arabidopsis thaliana* (NCBI Identifier No. gi 3080420). In the process of comparing the ESTs it was found that many of the clones had overlapping regions of homology. Using this homology it was possible to align the ESTs and assemble several contigs encoding unique corn, rice, soybean and wheat sugar transport proteins. The individual clones and the composition of each assembled contig are shown in Table 3. The BLAST results for each of the contigs and individual ESTs and are also shown in Table 3:

TABLE 3

BLAST Results for Clones Encoding Polypeptides Homologous to *Arabidopsis thaliana* Sugar Transport Protein

| Clone | BLAST pLog Score |
| --- | --- |
| Contig composed of clones:<br>p0032.crcba66r<br>p0097.cqran41r<br>cr1n.pk0143.h10<br>p0128.cpict38<br>p0106.cjlpm67r<br>cillc.pk001.f21<br>p0072.comgi92r<br>p0114.cimm181r | >250.00 |

TABLE 3-continued

BLAST Results for Clones Encoding Polypeptides Homologous
to *Arabidopsis thaliana* Sugar Transport Protein

| Clone | BLAST pLog Score |
|---|---|
| p0002.cgevb73r | |
| Contig composed of clones: | 27.70 |
| rlr12.pk0013.d11 | |
| rds1c.pk007.n17 | |
| rls6.pk0003.d5 | 54.00 |
| Contig composed of clones: | >250.00 |
| sgs4c.pk005.c9 | |
| sfl1.pk0079.a4 | |
| sdp3c.pk012.i1 | |
| ss1.pk0022.f1 | >250.00 |
| wlk8.pk0001.a12 | 21.30 |
| Contig composed of clones: | 149.00 |
| wlm96.pk043.e19 | |
| wre1n.pk0062.g6 | |
| wre1n.pk0006.b4 | 117.00 |

The sequence of the corn contig composed of clones p0032.crcba66r, p0097.cqran41r, cr1n.pk0143.h10, p0128.cpict38, p0106.cjlpm67r, cil1c.pk001.f21, p0072comgi92r, p0114.cimm181r and p0002.cgevb73r is shown in SEQ ID NO:1; the deduced amino acid sequence of this contig, which represents 100% of the protein, is shown in SEQ ID NO:2. A calculation of the percent similarity of the amino acid sequence set forth in SEQ ID NO:2 and the *Arabidopsis thaliana* sequence (using the Clustal algorithm) revealed that the protein encoded by SEQ ID NO:2 is 66% similar to the *Arabidopsis thaliana* sugar transport protein.

The sequence of the rice contig composed of clones rlr12.pk0013.d11 and rds1c.pk007.n17 is shown in SEQ ID NO:3; the deduced amino acid sequence of this contig, which represents 9% of the protein (N-terminal region), is shown in SEQ ID NO:4. A calculation of the percent similarity of the amino acid sequence set forth in SEQ ID NO:4 and the *Arabidopsis thaliana* sequence (using the Clustal algorithm) revealed that the protein encoded by SEQ ID NO:2 is 86% similar to the *Arabidopsis thaliana* sugar transport protein.

The sequence of the entire cDNA insert from clone rls6.pk0003.d5 is shown in SEQ ID NO:5; the deduced amino acid sequence of this cDNA, which represents 18% of the of the protein (C-terminal region), is shown in SEQ ID NO:6. A calculation of the percent similarity of the amino acid sequence set forth in SEQ ID NO:6 and the *Arabidopsis thaliana* sequence (using the Clustal algorithm) revealed that, the protein encoded by SEQ ID NO:6 is 74% similar to the *Arabidopsis thaliana* sugar transport protein.

The sequence of the soybean contig composed of clones sgs4c.pk005.c9, sfl1.pk0079.a4 and sdp3c.pk012.i1 is shown in SEQ ID NO:7; the deduced amino acid sequence of this contig, which represents 100% of the protein, is shown in SEQ ID NO:8. A calculation of the percent similarity of the amino acid sequence set forth in SEQ ID NO:8 and the *Arabidopsis thaliana* sequence (using the Clustal algorithm) revealed that the protein encoded by SEQ ID NO:8 is 68% similar to the *Arabidopsis thaliana* sugar transport protein.

The sequence of a portion of the cDNA insert from clone ss1.pk0022.f1 is shown in SEQ ID NO:9; the deduced amino acid sequence of this cDNA, which represents 66% of the of the protein (C-terminal region), is shown in SEQ ID NO:10. A calculation of the percent similarity of the amino acid sequence set forth in SEQ ID NO:10 and the *Arabidopsis thaliana* sequence (using the Clustal algorithm) revealed that the protein encoded by SEQ ID NO:10 is 66% similar to the *Arabidopsis thaliana* sugar transport protein.

The sequence of a portion of the cDNA insert from clone wlk8. pk0001.a12 is shown in SEQ ID NO:11; the deduced amino acid sequence of this cDNA, which represents 7% of the of the protein (N-terminal region), is shown in SEQ ID NO:12. A calculation of the percent similarity of the amino acid sequence set forth in SEQ ID NO:12 and the *Arabidopsis thaliana* sequence (using the Clustal algorithm) revealed that the protein encoded by SEQ ID NO:12 is 88% similar to the *Arabidopsis thaliana* sugar transport protein.

The sequence of the wheat contig composed of clones wlm96.pk043.e19 and wre1n.pk0062.g6 is shown in SEQ ID NO:13; the deduced amino acid sequence of this contig, which represents 45% of the protein (C-terminal region), is shown in SEQ ID NO:14. A calculation of the percent similarity of the amino acid sequence set forth in SEQ ID NO:14 and the *Arabidopsis thaliana* sequence (using the Clustal algorithm) revealed that the protein encoded by SEQ ID NO:14 is 65% similar to the *Arabidopsis thaliana* sugar transport protein.

The sequence of a portion of the cDNA insert from clone wre1n.pk0006.b4 is shown in SEQ ID NO:15; the deduced amino acid sequence of this cDNA, which represents 31% of the of the protein (C-terminal region), is shown in SEQ ID NO:16. A calculation of the percent similarity of the amino acid sequence set forth in SEQ ID NO:16 and the *Arabidopsis thaliana* sequence (using the Clustal algorithm) revealed that the protein encoded by SEQ ID NO:16 is 76% similar to the *Arabidopsis thaliana* sugar transport protein.

FIGS. 1A, 1B, 1C, 1D and 1E present an alignment of the amino acid sequence set forth in SEQ ID NOs:2, 4, 6, 8, 10, 12, 14 and 16 with the *Arabidopsis thaliana*-like sugar transport protein amino acid sequence, SEQ ID NO:29. Alignments were performed using the Clustal algorithm. The percent similarity between the corn, rice, soybean and wheat acid sequences was calculated to range between 16% to 89% using the Clustal algorithm.

BLAST scores and probabilities indicate that the instant nucleic acid fragments encode portions of sugar transport proteins. These sequences represent the first corn, rice, soybean and wheat sequences encoding *Arabidopsis thaliana*-like sugar transport proteins.

Example 4

Characterization of cDNA Clones Encoding *Beta vulgaris*-Like Sugar Transport Proteins The BLASTX search using the EST sequences from several corn, rice, soybean and wheat clones revealed similarity of the proteins encoded by the cDNAs,to a sugar transport protein from *Beta vulgaris* (NCBI Identifier No. gi 1778093). In the process of comparing the ESTs it was found that several of the rice and soybean clones had overlapping regions of homology. Using this homology it was possible to align the ESTs and assemble two contigs encoding unique rice and soybean *B. vulgaris*-like sugar transport proteins. The individual clones and the assembled composition of each contig are shown in Table 4. The BLAST results for each of the contigs and individual ESTs and are also shown in Table 4:

TABLE 4

BLAST Results for Clones Encoding Polypeptides Homologous to *Beta vulgaris* Sugar Transport Protein

| Clone | BLAST pLog Score |
|---|---|
| cc1.mn0002.h1 | 53.70 |
| cepe7.pk0018.g3 | 164.00 |
| Contig composed of clones:<br>rlr6.pk0005.b10<br>rl0n.pk102.p24<br>rl0n.pk107.p2 | >250.00 |
| Contig composed of clones:<br>sr1.pk0061.g8<br>sfl1.pk0058.h12<br>sgs2c.pk004.o17<br>sre.pk0032.h6 | >250.00 |
| wlk8.pk0001.a11 | >250.00 |
| wlm1.pk0012.h1 | >250.00 |

The sequence of a portion of the cDNA insert from clone cc1.mn0002.h1 is shown in SEQ ID NO:17; the deduced amino acid sequence of this cDNA, which represents 31% of the of the protein (N-terminal region), is shown in SEQ ID NO:18. A calculation of the percent similarity of the amino acid sequence set forth in SEQ ID NO:18 and the *Beta vulgaris* sequence (using the Clustal algorithm) revealed that the protein encoded by SEQ ID NO:18 is 65% similar to the *Beta vulgaris* sugar transport protein.

The sequence of the entire cDNA insert from clone cepe7.pk0018.g3 is shown in SEQ ID NO:19; the deduced amino acid sequence of this cDNA, which represents 100% of the of the protein, is shown in SEQ ID NO:20. A calculation of the percent similarity of the amino acid sequence set forth in SEQ ID NO:20 and the *Beta vulgaris* sequence (using the Clustal algorithm) revealed that the protein encoded by SEQ ID NO:20 is 57% similar to the *Beta vulgaris* sugar transport protein.

The sequence of the rice contig composed of clones rlr6.pk0005.b10, rl0n.pk102.p24 and rl0n.pk107.p2 is shown in SEQ ID NO:21; the deduced amino acid sequence of this contig, which represents 100% of the protein, is shown in SEQ ID NO:22. A calculation of the percent similarity of the amino acid sequence set forth in SEQ ID NO:22 and the *Beta vulgaris* sequence (using the Clustal algorithm) revealed that the protein encoded by SEQ ID NO:22 is 61% similar to the *Beta vulgaris* sugar transport protein.

The sequence of the soybean contig composed of clones sr1.pk0061.g8, sfl1.pk0058.h12, sgs2c.pk004.o17 and sre.pk0032.h6 is shown in SEQ ID NO:23; the deduced amino acid sequence of this contig, which represents 100% of the protein, is shown in SEQ ID NO:24. A calculation of the percent similarity of the amino acid sequence set forth in SEQ ID NO:24 and the *Beta vulgaris* sequence (using the Clustal algorithm) revealed that the protein encoded by SEQ ID NO:24 is 66% similar to the *Beta vulgaris* sugar transport protein.

The sequence of the entire cDNA insert from clone wlk8.pk0001.a11 is shown in SEQ ID NO:25; the deduced amino acid sequence of this cDNA, which represents 100% of the of the protein, is shown in SEQ ID NO:26. A calculation of the percent similarity of the amino acid sequence set forth in SEQ ID NO:26 and the *Beta vulgaris* sequence (using the Clustal algorithm) revealed that the protein encoded by SEQ ID NO:26 is 61% similar to the *Beta vulgaris* sugar transport protein.

The sequence of the entire cDNA insert from clone wlm1.pk0012.h1 is shown in SEQ ID NO:27; the deduced amino acid sequence of this cDNA, which represents 100% of the of the protein, is shown in SEQ ID NO:28. A calculation of the percent similarity of the amino acid sequence set forth in SEQ ID NO:28 and the *Beta vulgaris* sequence (using the Clustal algorithm) revealed that the protein encoded by SEQ ID NO:28 is 56% similar to the *Beta vulgaris* sugar transport protein.

FIGS. 2A, 2B, 2C end 2D present an alignment of the amino acid sequence set forth in SEQ ID NOs:18, 20, 22, 24, 26 and 28 with the *Beta vulgaris*-like sugar transport protein amino acid sequence, SEQ ID NO:30. Alignments were performed using the Clustal algorithm. The percent similarity between the corn, rice, soybean and wheat acid sequences was calculated to range between 43% to 81% using the Clustal algorithm.

BLAST scores and probabilities indicate that the instant nucleic acid fragments encode portions of sugar transport proteins. These sequences represent the first corn, rice, soybean and wheat sequences encoding *Beta vulgaris*-like sugar transport proteins.

Example 5

Expression of Chimeric Genes in Monocot Cells

A chimeric gene comprising a cDNA encoding sugar transport protein in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotide to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209). and bears accession number ATCC 97366, date of deposit Dec. 15, 1995. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coil* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding a sugar transport protein, and the 10 kD zeln 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al., (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833–839).

Example 6

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant sugar transport proteins in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising a sequence encoding a sugar transport protein. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Kline et al. (1987) *Nature* (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the sugar transport protein and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant sugar transport proteins can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the sugar transport protein are then screened for the correct orientation with respect to the T7 promoter by restriction enzyme analysis.

For high level expression, a plasmid clone with the cDNA insert in the correct orientation relative to the T7 promoter can be transformed into E. coli strain BL21 (DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthlo-□-galactoside, the inducer) can be added to a final concentration of 0.4 mM and incubation can be continued for 3 h at 25°. Cells are then harvested by centrifugation and re-suspended In 50 µL of 50 mM Tris-HCl (Tris(hydroxymethyl)aminomethane Hydrochloride) at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

What is claimed is:

1. An isolated nucleic acid fragment comprising:
   (a) a nucleotide sequence encoding a polypeptide having sugar transport protein activity, wherein said polypeptide is at least 90% identical to SEQ ID NO:20; or
   (b) the full-length complement of the nucleotide sequence of (a).

2. The isolated nucleic acid fragment of claim 1, wherein said polypeptide is at least 95% identical to SEQ ID NO:20.

3. The isolated nucleic acid fragment of claim 1, wherein the nucleotide sequence comprises SEQ ID NO:19.

4. A recombinant DNA construct comprising the isolated nucleic acid fragment of claim 1 operably linked to at least one regulatory sequence.

5. A vector comprising the isolated nucleic acid fragment of claim 1.

6. A method for transforming a cell, comprising transforming a cell with the recombinant DNA construct of claim 5.

7. A cell comprising the recombinant DNA construct of claim 4, wherein said cell is a microbial or a plant cell.

* * * * *

SEQUENCE LISTING

<160> NUMBER OF SEQ ID NOS: 30

<210> SEQ ID NO 1
<211> LENGTH: 2824
<212> TYPE: DNA
<213> ORGANISM: Zea mays
<220> FEATURE:
<221> NAME/KEY: unsure
<222> LOCATION: (29)
<221> NAME/KEY: unsure
<222> LOCATION: (622)
<221> NAME/KEY: unsure
<222> LOCATION: (636)
<221> NAME/KEY: unsure
<222> LOCATION: (638)

```
<221> NAME/KEY: unsure
<222> LOCATION: (669)
<221> NAME/KEY: unsure
<222> LOCATION: (771)
<221> NAME/KEY: unsure
<222> LOCATION: (822)
<221> NAME/KEY: unsure
<222> LOCATION: (856)
<221> NAME/KEY: unsure
<222> LOCATION: (889)
<221> NAME/KEY: unsure
<222> LOCATION: (896)
<221> NAME/KEY: unsure
<222> LOCATION: (944)

<400> SEQUENCE: 1 cccaccccccc tccactccac taccacggng gcacggcctg cctctgcagc tctgccctgc      60
tccgcaccccc tcgctctcca accccaacgc gcggcgttgc taaaattcac ctcagcgcgt     120
actccagttt ggccacctca ccacccgccg ccgctgttta agaaggcccc gcgcccgatc     180
ggggatcacg aaccttggcc gccgctgccg gagtggggggc gtagatttcc ggcggccatg     240
gggggcgccg tgatggtcgc catcgcggcc tctatcggca acttgctgca gggctgggac     300
aatgcgacaa ttgctggagc cgtcctgtac ataaagaagg aattcaacct gcagagcgag     360
cctctgatcg aaggcctcat cgtcgccatg ttcctcattg gggcaacagt catcacaaca     420
tctccggggc caagggctga ctgcgttggt aggaggccca tgctggtcgc ctcggctgtc     480
ctctacttcg tcagtgggct ggtgatgctt tgggcgccaa ttgtgtacat cttgctcctc     540
gcaaggctca ttgatgggtt cggtatcggt ttggcggtca cacttgttcc tctctacatc     600
tccgaaactg caccgcacag anattcttgg ggctgntnga acacgttgcc gcagttcatt     660
ggggtcagng gagggatgtt cctctcctac tgcatggtgt ttgggatgtc cctcatgccc     720
aaacctgatt ggaggctcat gcttggagtt ctgtcgatcc cgtcacttat ntactttgga     780
ctgactgtct tctacttgcc tgaatcacca aggtggcttg tnagcaaagg aaggatggcg     840
gaggcgaaga gagtgntgca aaggctgcgg ggaagagaag atgtctcang ggagangggct     900
cttctagttg aaggtttggg ggtcggtaaa gatacacgta tttnagagta catcattgga     960
cctgccaccg aggcagccga tgatcttgta actgacggtg ataaggaaca aatcacactt    1020
tatgggcctg aagaaggcca gtcatggatt gctcgacctt ctaagggacc catcatgctt    1080
ggaagtgtgc tttctcttgc atctcgtcat gggagcatgg tgaaccagag tgtacccctt    1140
atggatccga ttgtgacact ttttggtagt gtccatgaga atatgcctca agctggagga    1200
agtatgagga gcacattgtt tccaaacttt ggaagtatgt tcagtgtcac agatcagcat    1260
gccaaaaatg agcagtggga tgaagagaat cttcataggg atgacgagga gtacgcatct    1320
gatggtgcag gaggtgacta tgaggacaat ctccatagcc cattgctgtc caggcaggca    1380
acaggtgcgg aagggaagga cattgtgcac catggtcacc gtggaagtgc tttgagcatg    1440
agaaggcaaa gcctcttagg ggagggtgga gatggtgtga gcagcactga tatcggtggg    1500
ggatggcagc ttgcttggaa atggtcgagg aaggaaggtg agaatggtag aaaggaaggt    1560
ggtttcaaaa gagtctactt gcaccaagag ggagttcctg gctcaagaag gggctcaatt    1620
gtttcacttc ccggtggtgg cgatgttctt gagggtagtg agtttgtaca tgctgctgct    1680
ttagtaagtc agtcagcact tttctcaaag ggtcttgctg aaccacgcat gtcagatgct    1740
gccatggttc acccatctga ggtagctgcc aaaggttcac gttggaaaga tttgttttgaa    1800
cctggagtga ggcgtgccct gttagtcggt gttggaattc agatccttca acagtttgct    1860
```

-continued

```
ggaataaacg gtgttctgta ctataccccca caaattcttg agcaagctgg tgtggcagtt      1920
attctttcca aatttggtct cagctcggca tcagcatcca tcttgatcag ttctctcact      1980
accttactaa tgcttccttg cattggcttt gccatgctgc ttatggatct ttccggaaga      2040 aggttttgc tgctaggcac aattccaatc ttgatagcat ctctagttat cctggttgtg       2100
tccaatctaa ttgatttggg tacactagcc catgctttgc tctccaccat cagtgttatc      2160
gtctacttct gctgcttcgt tatgggattt ggtcccatcc ccaacatttt atgtgcagag      2220
atctttccaa ccagggttcg tggcctctgt attgccattt gtgcctttac attctggatc      2280
ggagatatca tcgtcaccta cagccttcct gtgatgctga atgctattgg actggcgggt      2340
gttttcagca tatatgcagt cgtatgcttg atttcctttg tgttcgtctt ccttaaggtc      2400
cctgagacaa aggggatgcc ccttgaggtt attaccgaat tctttgcagt tggtgcgaag      2460
caagcggctg caaaagccta atttctttgg tacctttgtg tgcaactatt gcactgtaag      2520
ttagaaactt gaaggggttt caccaagaag ctcggagaat tactttggat ttgtgtaaat      2580
gttaagggaa cgaacatctg ctcatgctcc tcaaacggta aaaagagtc cctcaatggc       2640 aaataggagt cgttaagttg tcaatgtcat ttaccatatg ttttacctat ttgtactgta      2700
ttataagtca agctattcaa cgctggttgt tgctagaaat ctttagaaca aagatgataa      2760
tgatctgatc tgatgttata atattcaaat ctcaaataaa gaaatatcg tttctcaaaa       2820 aaaa                                                                    2824
```

```
<210> SEQ ID NO 2
<211> LENGTH: 747
<212> TYPE: PRT
<213> ORGANISM: Zea mays
<220> FEATURE:
<221> NAME/KEY: UNSURE
<222> LOCATION: (129)
<221> NAME/KEY: UNSURE
<222> LOCATION: (133)..(134)
<221> NAME/KEY: UNSURE
<222> LOCATION: (144)
<221> NAME/KEY: UNSURE
<222> LOCATION: (178)
<221> NAME/KEY: UNSURE
<222> LOCATION: (207)
<221> NAME/KEY: UNSURE
<222> LOCATION: (218)
<221> NAME/KEY: UNSURE
<222> LOCATION: (220)
<221> NAME/KEY: UNSURE
<222> LOCATION: (236)

<400> SEQUENCE: 2

Met Gly Gly Ala Val Met Val Ala Ile Ala Ala Ser Ile Gly Asn Leu
 1               5                  10                  15

Leu Gln Gly Trp Asp Asn Ala Thr Ile Ala Gly Ala Val Leu Tyr Ile
                20                  25                  30

Lys Lys Glu Phe Asn Leu Gln Ser Glu Pro Leu Ile Glu Gly Leu Ile
            35                  40                  45

Val Ala Met Phe Leu Ile Gly Ala Thr Val Ile Thr Thr Ser Pro Gly
        50                  55                  60

Pro Arg Ala Asp Cys Val Gly Arg Arg Pro Met Leu Val Ala Ser Ala
 65                 70                  75                  80

Val Leu Tyr Phe Val Ser Gly Leu Val Met Leu Trp Ala Pro Ile Val
                85                  90                  95

Tyr Ile Leu Leu Leu Ala Arg Leu Ile Asp Gly Phe Gly Ile Gly Leu
            100                 105                 110
```

```
Ala Val Thr Leu Val Pro Leu Tyr Ile Ser Glu Thr Ala Pro His Arg
        115                 120                 125

Xaa Ser Trp Gly Xaa Xaa Asn Thr Leu Pro Gln Phe Ile Gly Val Xaa
    130                 135                 140

Gly Gly Met Phe Leu Ser Tyr Cys Met Val Phe Gly Met Ser Leu Met
145                 150                 155                 160

Pro Lys Pro Asp Trp Arg Leu Met Leu Gly Val Leu Ser Ile Pro Ser
                165                 170                 175

Leu Xaa Tyr Phe Gly Leu Thr Val Phe Tyr Leu Pro Glu Ser Pro Arg
        180                 185                 190

Trp Leu Val Ser Lys Gly Arg Met Ala Glu Ala Lys Arg Val Xaa Gln
        195                 200                 205

Arg Leu Arg Gly Arg Glu Asp Val Ser Xaa Glu Xaa Ala Leu Leu Val
        210                 215                 220

Glu Gly Leu Gly Val Gly Lys Asp Thr Arg Ile Xaa Glu Tyr Ile Ile
225                 230                 235                 240

Gly Pro Ala Thr Glu Ala Ala Asp Asp Leu Val Thr Asp Gly Asp Lys
                245                 250                 255

Glu Gln Ile Thr Leu Tyr Gly Pro Glu Glu Gly Gln Ser Trp Ile Ala
                260                 265                 270

Arg Pro Ser Lys Gly Pro Ile Met Leu Gly Ser Val Leu Ser Leu Ala
            275                 280                 285

Ser Arg His Gly Ser Met Val Asn Gln Ser Val Pro Leu Met Asp Pro
    290                 295                 300

Ile Val Thr Leu Phe Gly Ser Val His Glu Asn Met Pro Gln Ala Gly
305                 310                 315                 320

Gly Ser Met Arg Ser Thr Leu Phe Pro Asn Phe Gly Ser Met Phe Ser
                325                 330                 335

Val Thr Asp Gln His Ala Lys Asn Glu Gln Trp Asp Glu Glu Asn Leu
                340                 345                 350

His Arg Asp Asp Glu Glu Tyr Ala Ser Asp Gly Ala Gly Gly Asp Tyr
            355                 360                 365

Glu Asp Asn Leu His Ser Pro Leu Leu Ser Arg Gln Ala Thr Gly Ala
        370                 375                 380

Glu Gly Lys Asp Ile Val His His Gly His Arg Gly Ser Ala Leu Ser
385                 390                 395                 400

Met Arg Arg Gln Ser Leu Leu Gly Glu Gly Gly Asp Gly Val Ser Ser
                405                 410                 415

Thr Asp Ile Gly Gly Gly Trp Gln Leu Ala Trp Lys Trp Ser Glu Lys
            420                 425                 430

Glu Gly Glu Asn Gly Arg Lys Glu Gly Phe Lys Arg Val Tyr Leu
            435                 440                 445

His Gln Glu Gly Val Pro Gly Ser Arg Gly Ser Ile Val Ser Leu
    450                 455                 460

Pro Gly Gly Gly Asp Val Leu Glu Gly Ser Glu Phe Val His Ala Ala
465                 470                 475                 480

Ala Leu Val Ser Gln Ser Ala Leu Phe Ser Lys Gly Leu Ala Glu Pro
                485                 490                 495

Arg Met Ser Asp Ala Ala Met Val His Pro Ser Glu Val Ala Ala Lys
            500                 505                 510

Gly Ser Arg Trp Lys Asp Leu Phe Glu Pro Gly Val Arg Arg Ala Leu
            515                 520                 525
```

Leu Val Gly Val Gly Ile Gln Ile Leu Gln Gln Phe Ala Gly Ile Asn
    530                 535                 540

Gly Val Leu Tyr Tyr Thr Pro Gln Ile Leu Glu Gln Ala Gly Val Ala
545                 550                 555                 560

Val Ile Leu Ser Lys Phe Gly Leu Ser Ser Ala Ser Ala Ser Ile Leu
                565                 570                 575

Ile Ser Ser Leu Thr Thr Leu Leu Met Leu Pro Cys Ile Gly Phe Ala
            580                 585                 590

Met Leu Leu Met Asp Leu Ser Gly Arg Arg Phe Leu Leu Leu Gly Thr
        595                 600                 605

Ile Pro Ile Leu Ile Ala Ser Leu Val Ile Leu Val Val Ser Asn Leu
    610                 615                 620

Ile Asp Leu Gly Thr Leu Ala His Ala Leu Leu Ser Thr Ile Ser Val
625                 630                 635                 640

Ile Val Tyr Phe Cys Cys Phe Val Met Gly Phe Gly Pro Ile Pro Asn
                645                 650                 655

Ile Leu Cys Ala Glu Ile Phe Pro Thr Arg Val Arg Gly Leu Cys Ile
            660                 665                 670

Ala Ile Cys Ala Phe Thr Phe Trp Ile Gly Asp Ile Ile Val Thr Tyr
        675                 680                 685

Ser Leu Pro Val Met Leu Asn Ala Ile Gly Leu Ala Gly Val Phe Ser
    690                 695                 700

Ile Tyr Ala Val Val Cys Leu Ile Ser Phe Val Phe Val Phe Leu Lys
705                 710                 715                 720

Val Pro Glu Thr Lys Gly Met Pro Leu Glu Val Ile Thr Glu Phe Phe
                725                 730                 735

Ala Val Gly Ala Lys Gln Ala Ala Ala Lys Ala
            740                 745

<210> SEQ ID NO 3
<211> LENGTH: 443
<212> TYPE: DNA
<213> ORGANISM: Oryza sativa
<220> FEATURE:
<221> NAME/KEY: unsure
<222> LOCATION: (193)
<221> NAME/KEY: unsure
<222> LOCATION: (388)
<221> NAME/KEY: unsure
<222> LOCATION: (435)
<221> NAME/KEY: unsure
<222> LOCATION: (439)

<400> SEQUENCE: 3
gaagagctca ccccccccc ctcggccctg gactccctcc tccaaatctc ccctaaaagc        60
ttcccaattt ggcgagaatt ccccatatat ttgccccatc tcggcgtccc aacgagccct       120
tccagattcc cagccgcctc tcttcttgtt aggggatccg aaatctcggt ggacgagaga       180
cttggtggta atnattcgcc ggccatggcg ggcgccgtgc tggtcgccat cgcggcctcc       240
atcggcaact tgctgcaggg ctgggataat gcaaccattg caggtgcggt actgtacatc       300
aagaaggaat tcaacttgca tagcgacccc cttatcgaag gtctgatcgt ggccatgtcg       360
ctcattgggg ccaccatcat cacgacgntc tctgcgagca ggtggctgac tcttttggta       420
tggcggccca tgctnatcnc ttc                                              443

<210> SEQ ID NO 4
<211> LENGTH: 131
<212> TYPE: PRT

<213> ORGANISM: Oryza sativa
<220> FEATURE:
<221> NAME/KEY: UNSURE
<222> LOCATION: (65)
<221> NAME/KEY: UNSURE
<222> LOCATION: (130)

<400> SEQUENCE: 4

Glu Glu Leu Thr Pro Pro Pro Ser Ala Leu Asp Ser Leu Leu Gln Ile
1               5                   10                  15

Ser Pro Lys Ser Phe Pro Ile Trp Arg Glu Phe Pro Ile Tyr Leu Pro
            20                  25                  30

His Leu Gly Val Pro Thr Ser Pro Ser Arg Phe Pro Ala Ala Ser Leu
        35                  40                  45

Leu Val Arg Gly Ser Glu Ile Ser Val Asp Glu Arg Leu Gly Gly Asn
    50                  55                  60

Xaa Ser Pro Ala Met Ala Gly Ala Val Leu Val Ala Ile Ala Ala Ser
65                  70                  75                  80

Ile Gly Asn Leu Leu Gln Gly Trp Asp Asn Ala Thr Ile Ala Gly Ala
                85                  90                  95

Val Leu Tyr Ile Lys Lys Glu Phe Asn Leu His Ser Asp Pro Leu Ile
            100                 105                 110

Glu Gly Leu Ile Val Ala Met Ser Leu Ile Gly Ala Thr Ile Ile Thr
        115                 120                 125

Thr Xaa Ser
    130

<210> SEQ ID NO 5
<211> LENGTH: 870
<212> TYPE: DNA
<213> ORGANISM: Oryza sativa

<400> SEQUENCE: 5
gcacgaggtt ctaaccttga ttctggtcaa tattctggat gtggggacca tggttcatgc    60
ctcactgtcc acagtcagtg tcatactcta cttctgcttc tttgtcatgg ggttcgggcc   120
tattccaaac attctctgtg cagagatttt cccgaccacc gttcgtggca tctgcatagc   180
catctgtgcc ctaacattct ggatcggtga tatcattgtg acatacaccc tccccgtgat   240
gctcaacgcc attggactcg ctggagtgtt tggaatctac gcagtggtct gcatactggc   300
tttcctgttt gtcttcatga aggtgccgga gacaaagggc atgcctcttg aagtcatcac   360
cgagttcttc tctgtcggag caaagcaggc caaggaggac tagttgctcg atcaagtga   420
tcaatcagat tgctggtggt aattttgttg cttccaaatc gcgctgcggg ttaaacctgt   480
gatggatgct tgttaaaga atcttggaag agatcaaaat gcagtgagcc taagagatg    540
atttggctgt acatcatgag ctgaatcct gtcgtagact ggattttgga gcttaggata   600
tgtagatcat ctgttccttt tggtttggtc attttccatt tgtgtttctt tggaattctt   660
ctccctgtaa ctagtggtct atcacagttg tgttactggt tttgccttac tcttgagttt   720
gttttcttct ctcggttgtg agttctgaat attagcatag ccgagtacta gttctgaatt   780
ggtttcctct ctgctgaaca tctttcattg atgcttggat tcatcaaaa aaaaaaaaa    840
aaaactcgag ggggagcccg gtacacatct                                   870

<210> SEQ ID NO 6
<211> LENGTH: 131
<212> TYPE: PRT
<213> ORGANISM: Oryza sativa

```
<400> SEQUENCE: 6

Val Leu Thr Leu Ile Leu Val Asn Ile Leu Asp Val Gly Thr Met Val
 1               5                  10                  15

His Ala Ser Leu Ser Thr Val Ser Val Ile Leu Tyr Phe Cys Phe Phe
            20                  25                  30

Val Met Gly Phe Gly Pro Ile Pro Asn Ile Leu Cys Ala Glu Ile Phe
        35                  40                  45

Pro Thr Thr Val Arg Gly Ile Cys Ile Ala Ile Cys Ala Leu Thr Phe
    50                  55                  60

Trp Ile Gly Asp Ile Ile Val Thr Tyr Thr Leu Pro Val Met Leu Asn
65                  70                  75                  80

Ala Ile Gly Leu Ala Gly Val Phe Gly Ile Tyr Ala Val Val Cys Ile
                85                  90                  95

Leu Ala Phe Leu Phe Val Phe Met Lys Val Pro Glu Thr Lys Gly Met
            100                 105                 110

Pro Leu Glu Val Ile Thr Glu Phe Phe Ser Val Gly Ala Lys Gln Ala
        115                 120                 125

Lys Glu Asp
    130

<210> SEQ ID NO 7
<211> LENGTH: 2601
<212> TYPE: DNA
<213> ORGANISM: Glycine max

<400> SEQUENCE: 7
gttgcttaac ccttgttgag tgaagtgagc aaggggaatg gcgatctgaa attcggatac    60
tttaattgct tctcgctttc accgaccgaa ctcaatttat agatactccg tcaacctcaa   120
tcccaactaa ctagcagttc cttgctgctg ctccttcttc accatatcgc agtaatgaaa   180
ggtgccgtcc ttgttgctat tgccgcttcc attggtaatt tcctccaagg atgggataat   240
gctaccatcg ccggggctaa tggttacatt aagaaagacc ttgctttggg aacaactatg   300
gaaaggcttg tggtgggcat gtccctgatt ggagcaacgg taatcaccac atgctctggt   360
cctatagcgg attggctcgg tcggcgaccc atgatgataa tctcatctgt gctctatttc   420
ttgggtggtt tggtgatgct gtggtcccca aatgtgtatg tgttgtgctt ggcgaggcta   480
cttgatggat ttgggattgg ccttgctgtg actcttgtcc cggtctatat atctgaaacg   540
gcgccgtctg aaataagggg gtcgttgaat acgcttcctc agttcagtgg ctctggagga   600 atgttttttgt cgtactgtat ggttttttggc atgtcattga gtcccgcgcc tagctggagg   660
ctcatgcttg gggttctgtc tattccttct ctcttgtatt ttgcattgac catttttttc   720
ttgcccgagt ctcctcggtg gctggtcagc aaaggaagga tgctcgaggc taagaaggtg   780
ctccaaagat tgcgcggaag ggaggatgtg tcaggcgaga tggcattgct ggttgaaggt   840
ctcgggattg ggggtgatac atctatcgaa gagtacataa ttggccctgc tgacgatgtg   900
gctgatggtc atgaacatgc aacagagaaa gataaaattc gattatatgg atcccaagca   960
ggcctttctt ggttatcaaa acctgtcact ggacagagtt ctattggcct tgcgtcacac  1020
catgaagcca tcatcaacca aagcatgccc tcatggatcc tctggtgac actgtttggt  1080 agcattcatg agaagctccc cgagacagga gcaagaggaa gcatgcgaag cactctgttt  1140
ccaaattttg gaagcatgtt cagcactgct gagccgcatg ctaaaattga acaatgggat  1200
gaagaaagct acaaagggaa acgtgaggac tacatgtcag atgcaacccg tggggactcc  1260
```

-continued

| | |
|---|---|
| gatgataatt tgcacagtcc tttaatctca cgccaaacaa caagccttga aaaagactta | 1320 |
| cctcctcctc cttcccatgg cagtatcctt ggcagcatga ggcgtcacag tagtctcatg | 1380 |
| caagggtcag gtgagcaagg tggtagtaca ggtattggtg gtggctggca actggcatgg | 1440 |
| aaatggactg ataaaggtga ggatggaaaa caacaaggag ggtttaaaag gatttattta | 1500 |
| catgaggagg gagtttctgc atctcgtcgt ggatccattg tatcgattcc cggtgaaggc | 1560 |
| gaatttgtcc aggctgctgc cttggtaagc caacccgctc tttactccaa ggagcttatt | 1620 |
| gatggacacc cagttgggcc tgcaatggtt cacccatctg agacagcttc aaaggggcca | 1680 |
| agttggaaag ctcttcttga accaggggtt aagcatgcat ggttgttgg agttggaata | 1740 |
| caaatacttc agcagttttc agggataaat ggggttctat attacacacc tcaaatcctt | 1800 |
| gaagaggccg tgttgaagt tcttctttca gatataggca ttggctcaga gtcggcatca | 1860 |
| ttccttatca gtgctttcac aaccttcttg atgcttccct gtataggcgt agccatgaag | 1920 |
| ctcatggatg tttcaggcag aaggcagttg ctacttacta caatcccccgt gctgattgtg | 1980 |
| tcactcatta ttttggtcat tggaagcctg gtaaattttg caatgtcgc ccatgcagca | 2040 |
| atctcaacag tatgcgttgt ggtttatttc tgctgctttg tgatgggtta tggaccaatt | 2100 |
| ccaaacatcc tttgctcaga gattttcccc actagggtgc gtggcctctg cattgctatc | 2160 |
| tgtgcattag tgttctggat ggagacatc atcatcacat actcgctgcc tgtgatgctc | 2220 |
| ggctctttag gacttggtgg tgtattcgcc atttacgcag ttgtttgttt catctcgtgg | 2280 |
| atatttgtgt ttttgaaggt tccagaaaca aagggcatgc cccttgaagt catctctgaa | 2340 |
| ttcttttctg ttggagcaaa gcaggctgct tctgccaaga atgagtgaca caacacaagt | 2400 |
| ccgttatata ctctgtaact ttagttgtta agccatcat ctctcgtctt tacagatttt | 2460 |
| gcttttcata agtttatttg gaggaagata ttttgaaaca tatgggtttt tttttctttc | 2520 |
| ataaaaataa aacccttccc ttttgggtg gggaaaagaa aaaaaaaaa aaaaaaaaa | 2580 |
| aaaaaaaaa aaaaaaaaa a | 2601 |

<210> SEQ ID NO 8
<211> LENGTH: 737
<212> TYPE: PRT
<213> ORGANISM: Glycine max

<400> SEQUENCE: 8

Met Lys Gly Ala Val Leu Val Ala Ile Ala Ala Ser Ile Gly Asn Phe
1               5                   10                  15

Leu Gln Gly Trp Asp Asn Ala Thr Ile Ala Gly Ala Asn Gly Tyr Ile
            20                  25                  30

Lys Lys Asp Leu Ala Leu Gly Thr Thr Met Glu Arg Leu Val Val Gly
        35                  40                  45

Met Ser Leu Ile Gly Ala Thr Val Ile Thr Thr Cys Ser Gly Pro Ile
    50                  55                  60

Ala Asp Trp Leu Gly Arg Arg Pro Met Met Ile Ile Ser Ser Val Leu
65                  70                  75                  80

Tyr Phe Leu Gly Gly Leu Val Met Leu Trp Ser Pro Asn Val Tyr Val
            85                  90                  95

Leu Cys Leu Ala Arg Leu Leu Asp Gly Phe Gly Ile Gly Leu Ala Val
            100                 105                 110

Thr Leu Val Pro Val Tyr Ile Ser Glu Thr Ala Pro Ser Glu Ile Arg
        115                 120                 125

```
Gly Ser Leu Asn Thr Leu Pro Gln Phe Ser Gly Ser Gly Met Phe
    130                 135                 140
Leu Ser Tyr Cys Met Val Phe Gly Met Ser Leu Ser Pro Ala Pro Ser
145                 150                 155                 160
Trp Arg Leu Met Leu Gly Val Leu Ser Ile Pro Ser Leu Leu Tyr Phe
                165                 170                 175
Ala Leu Thr Ile Phe Phe Leu Pro Glu Ser Pro Arg Trp Leu Val Ser
            180                 185                 190
Lys Gly Arg Met Leu Glu Ala Lys Lys Val Leu Gln Arg Leu Arg Gly
        195                 200                 205
Arg Glu Asp Val Ser Gly Glu Met Ala Leu Leu Val Glu Gly Leu Gly
    210                 215                 220
Ile Gly Gly Asp Thr Ser Ile Glu Glu Tyr Ile Ile Gly Pro Ala Asp
225                 230                 235                 240
Asp Val Ala Asp Gly His Glu His Ala Thr Glu Lys Asp Lys Ile Arg
                245                 250                 255
Leu Tyr Gly Ser Gln Ala Gly Leu Ser Trp Leu Ser Lys Pro Val Thr
            260                 265                 270
Gly Gln Ser Ser Ile Gly Leu Ala Ser His His Gly Ser Ile Ile Asn
        275                 280                 285
Gln Ser Met Pro Leu Met Asp Pro Leu Val Thr Leu Phe Gly Ser Ile
    290                 295                 300
His Glu Lys Leu Pro Glu Thr Gly Ala Arg Gly Ser Met Arg Ser Thr
305                 310                 315                 320
Leu Phe Pro Asn Phe Gly Ser Met Phe Ser Thr Ala Glu Pro His Ala
                325                 330                 335
Lys Ile Glu Gln Trp Asp Glu Ser Leu Gln Arg Glu Arg Glu Asp
            340                 345                 350
Tyr Met Ser Asp Ala Thr Arg Gly Asp Ser Asp Asn Leu His Ser
        355                 360                 365
Pro Leu Ile Ser Arg Gln Thr Thr Ser Leu Glu Lys Asp Leu Pro Pro
    370                 375                 380
Pro Pro Ser His Gly Ser Ile Leu Gly Ser Met Arg Arg His Ser Ser
385                 390                 395                 400
Leu Met Gln Gly Ser Gly Glu Gln Gly Gly Ser Thr Gly Ile Gly Gly
                405                 410                 415
Gly Trp Gln Leu Ala Trp Lys Trp Thr Asp Lys Gly Glu Asp Gly Lys
            420                 425                 430
Gln Gln Gly Gly Phe Lys Arg Ile Tyr Leu His Glu Glu Gly Val Ser
        435                 440                 445
Ala Ser Arg Arg Gly Ser Ile Val Ser Ile Pro Gly Glu Gly Glu Phe
    450                 455                 460
Val Gln Ala Ala Ala Leu Val Ser Gln Pro Ala Leu Tyr Ser Lys Glu
465                 470                 475                 480
Leu Ile Asp Gly His Pro Val Gly Pro Ala Met Val His Pro Ser Glu
                485                 490                 495
Thr Ala Ser Lys Gly Pro Ser Trp Lys Ala Leu Leu Glu Pro Gly Val
            500                 505                 510
Lys His Ala Leu Val Val Gly Val Gly Ile Gln Ile Leu Gln Gln Phe
        515                 520                 525
Ser Gly Ile Asn Gly Val Leu Tyr Tyr Thr Pro Gln Ile Leu Glu Glu
    530                 535                 540
Ala Gly Val Glu Val Leu Leu Ser Asp Ile Gly Ile Gly Ser Glu Ser
```

```
                545                 550                 555                 560
Ala Ser Phe Leu Ile Ser Ala Phe Thr Thr Phe Leu Met Leu Pro Cys
                    565                 570                 575
Ile Gly Val Ala Met Lys Leu Met Asp Val Ser Gly Arg Arg Gln Leu
                580                 585                 590
Leu Leu Thr Thr Ile Pro Val Leu Ile Val Ser Leu Ile Ile Leu Val
            595                 600                 605
Ile Gly Ser Leu Val Asn Phe Gly Asn Val Ala His Ala Ala Ile Ser
        610                 615                 620
Thr Val Cys Val Val Tyr Phe Cys Cys Phe Val Met Gly Tyr Gly
625                 630                 635                 640
Pro Ile Pro Asn Ile Leu Cys Ser Glu Ile Phe Pro Thr Arg Val Arg
                645                 650                 655
Gly Leu Cys Ile Ala Ile Cys Ala Leu Val Phe Trp Ile Gly Asp Ile
                660                 665                 670
Ile Ile Thr Tyr Ser Leu Pro Val Met Leu Gly Ser Leu Gly Leu Gly
            675                 680                 685
Gly Val Phe Ala Ile Tyr Ala Val Val Cys Phe Ile Ser Trp Ile Phe
        690                 695                 700
Val Phe Leu Lys Val Pro Glu Thr Lys Gly Met Pro Leu Glu Val Ile
705                 710                 715                 720
Ser Glu Phe Phe Ser Val Gly Ala Lys Gln Ala Ala Ser Ala Lys Asn
                725                 730                 735
Glu

<210> SEQ ID NO 9
<211> LENGTH: 1692
<212> TYPE: DNA
<213> ORGANISM: Glycine max

<400> SEQUENCE: 9
gcacgaggga tccgtccaga gaaaaagatc aaattaagtt gtatggacca gaacaaggcc      60
agtcctgggt tgctagacct gttgctggac caaattctgt tggccttgta tctaggaaag     120
gaagcatggc aaatccaagc agtctagtgg accctctagt gaccctcttt ggtagtgtac     180
atgagaagct cccagaaaca ggaagcaccc ttttccaca cttttgggagt atgttcagtg     240
ttgggggaaa tcagccaagg aatgaagatt gggatgagga agcctagcc agagagggtg     300
atgattatgt ctctgatgct ggtgattctg atgacaattt gcagagtcca ttgatctcac     360
gtcaaacaac gagtctggat aaggacatac ctcctcatgc ccatagtaac cttgcaagca     420
tgaggcaagg tagtcttta catggaaatt caggagaacc cactggtagt actgggattg     480
gtggtggttg gcagctagca tggaaatggt ctgaaagaga gggcccagat ggaaagaagg     540
aaggtggctt caagagaata tatttacacc aagatggtgg ttctggatct agacgtgggt     600
ctgtggtttc actccctggc ggtgatttac caactgacag tgaggttgta caggctgctg     660
ctctggtgag tcagcctgcc ctttataatg aggccttat gcgtcaacgg ccagttggac     720
cagctatgat tcatccctct gaaacaattg caaaagggcc aagttggagt gatcttttg     780
aacctggggt gaagcatgca ttgattgtgg ggtgggaat gcaaattctt cagcagttct     840
ctggtataaa tgggtcctc tactatacgc tcaaattct tgagcaggca ggtgttggtt     900
atcttctttc aagcctaggc cttgttcta cttcttcatc ctttcttatt agtgcggtga     960
caaccttgtt gatgcttcct tgtatagcca ttgccatgag gctcatggat atttcaggca    1020
```

-continued

```
gaaggacttt gctgctcagt acaatccccg tcctaatagc agctcttctc atattagtcc    1080
tgggaagtct tgtggatttg ggatccactg caaatgcatc aatctcaacc attagtgtta    1140
ttgtctattt ctgtttcttt gtcatgggat ttggaccaat tcctaatata ctttgtgcag    1200
agatcttccc cactcgagtt cgtggtctct gcattgctat ttgtgccctt acctttggga    1260
tctgtgatat cattgtcacc tacacactcc cagttatgct caattctgta ggcctcgctg    1320 gtgttttttgg tatttatgct gtcgtgtgct tcatagcatg ggtgtttgtc tttttgaaag    1380
ttccagaaac caagggcatg ccactggaag tgatcattga gttcttctct gtcggagcaa    1440
aacagtttga cgatgccaag cacaactgac ccaaggacat gataaattca agttttgac     1500 ggtaccttct aattattttc aatctacggc tgtttgaaat tttcccctct tttaaaattt    1560
tattttctat ttattctctc ttttccgtgg gttgagatta agaaacaaga aactttgttt    1620
ctgtaaagaa aaatgttcat tttctggttc atttatggaa ctttatatac ttcctaaaaa    1680
aaaaaaaaaa aa                                                        1692
```

```
<210> SEQ ID NO 10
<211> LENGTH: 486
<212> TYPE: PRT
<213> ORGANISM: Glycine max

<400> SEQUENCE: 10

Asp Pro Ser Arg Glu Lys Asp Gln Ile Lys Leu Tyr Gly Pro Glu Gln
 1               5                  10                  15

Gly Gln Ser Trp Val Ala Arg Pro Val Ala Gly Pro Asn Ser Val Gly
            20                  25                  30

Leu Val Ser Arg Lys Gly Ser Met Ala Asn Pro Ser Ser Leu Val Asp
        35                  40                  45

Pro Leu Val Thr Leu Phe Gly Ser Val His Glu Lys Leu Pro Glu Thr
    50                  55                  60

Gly Ser Thr Leu Phe Pro His Phe Gly Ser Met Phe Ser Val Gly Gly
65                  70                  75                  80

Asn Gln Pro Arg Asn Glu Asp Trp Asp Glu Glu Ser Leu Ala Arg Glu
                85                  90                  95

Gly Asp Asp Tyr Val Ser Asp Ala Gly Asp Ser Asp Asp Asn Leu Gln
            100                 105                 110

Ser Pro Leu Ile Ser Arg Gln Thr Thr Ser Leu Asp Lys Asp Ile Pro
        115                 120                 125

Pro His Ala His Ser Asn Leu Ala Ser Met Arg Gln Gly Ser Leu Leu
    130                 135                 140

His Gly Asn Ser Gly Glu Pro Thr Gly Ser Thr Gly Ile Gly Gly Gly
145                 150                 155                 160

Trp Gln Leu Ala Trp Lys Trp Ser Glu Arg Glu Gly Pro Asp Gly Lys
                165                 170                 175

Lys Glu Gly Gly Phe Lys Arg Ile Tyr Leu His Gln Asp Gly Gly Ser
            180                 185                 190

Gly Ser Arg Arg Gly Ser Val Val Ser Leu Pro Gly Gly Asp Leu Pro
        195                 200                 205

Thr Asp Ser Glu Val Val Gln Ala Ala Leu Val Ser Gln Pro Ala
    210                 215                 220

Leu Tyr Asn Glu Asp Leu Met Arg Gln Arg Pro Val Gly Pro Ala Met
225                 230                 235                 240

Ile His Pro Ser Glu Thr Ile Ala Lys Gly Pro Ser Trp Ser Asp Leu
                245                 250                 255
```

-continued

```
Phe Glu Pro Gly Val Lys His Ala Leu Ile Val Gly Val Gly Met Gln
            260                 265                 270

Ile Leu Gln Gln Phe Ser Gly Ile Asn Gly Val Leu Tyr Tyr Thr Pro
        275                 280                 285

Gln Ile Leu Glu Gln Ala Gly Val Gly Tyr Leu Leu Ser Ser Leu Gly
    290                 295                 300

Leu Gly Ser Thr Ser Ser Ser Phe Leu Ile Ser Ala Val Thr Thr Leu
305                 310                 315                 320

Leu Met Leu Pro Cys Ile Ala Ile Ala Met Arg Leu Met Asp Ile Ser
                325                 330                 335

Gly Arg Arg Thr Leu Leu Ser Thr Ile Pro Val Leu Ile Ala Ala
            340                 345                 350

Leu Leu Ile Leu Val Leu Gly Ser Leu Val Asp Leu Gly Ser Thr Ala
        355                 360                 365

Asn Ala Ser Ile Ser Thr Ile Ser Val Ile Val Tyr Phe Cys Phe Phe
    370                 375                 380

Val Met Gly Phe Gly Pro Ile Pro Asn Ile Leu Cys Ala Glu Ile Phe
385                 390                 395                 400

Pro Thr Arg Val Arg Gly Leu Cys Ile Ala Ile Cys Ala Leu Thr Phe
                405                 410                 415

Trp Ile Cys Asp Ile Ile Val Thr Tyr Thr Leu Pro Val Met Leu Asn
            420                 425                 430

Ser Val Gly Leu Ala Gly Val Phe Gly Ile Tyr Ala Val Val Cys Phe
        435                 440                 445

Ile Ala Trp Val Phe Val Phe Leu Lys Val Pro Glu Thr Lys Gly Met
    450                 455                 460

Pro Leu Glu Val Ile Ile Glu Phe Phe Ser Val Gly Ala Lys Gln Phe
465                 470                 475                 480

Asp Asp Ala Lys His Asn
                485
```

<210> SEQ ID NO 11
<211> LENGTH: 510
<212> TYPE: DNA
<213> ORGANISM: Triticum aestivum
<220> FEATURE:
<221> NAME/KEY: unsure
<222> LOCATION: (421)
<221> NAME/KEY: unsure
<222> LOCATION: (434)
<221> NAME/KEY: unsure
<222> LOCATION: (441)
<221> NAME/KEY: unsure
<222> LOCATION: (458)
<221> NAME/KEY: unsure
<222> LOCATION: (483)
<221> NAME/KEY: unsure
<222> LOCATION: (493)
<221> NAME/KEY: unsure
<222> LOCATION: (498)

<400> SEQUENCE: 11

```
cggtggcagc cggggcagtg aaggaggggt agctcttggc tcctatttga ggcggcttcg      60
ctcggttctg atctaccgca ccacaccacc acaccacacc aggggcctgc cgcttcttgg     120
gcttctccat ctcatctcct tggttggttc tctactagag aggcgcagct gcagggatcc     180
ttggtggaga ggagggaaga agatgtcggg tgctgcactg gtcgcgattg cggcttccat     240
tggcaatctg ctgcaggggt gggacaatgc caccatcgct ggtgctgttc tgtacatcaa     300
```

```
gaaggaattc cagctcgaaa ataatccgac tgtggagggg ctcatcgtgg catgtcctca      360
tcgggtgcaa catcatcaca cattctccgg gccagtatca aactggggttg ccgggcccta     420 ngccatctcc ttgntttcaa ntcccaaggg ctaatcanct aggcaccaat gtcaatgtgc      480
gcnccggaac ctntcaaagg ttggaacgtt                                       510

<210> SEQ ID NO 12
<211> LENGTH: 117
<212> TYPE: PRT
<213> ORGANISM: Triticum aestivum

<400> SEQUENCE: 12

Gly Gly Ser Arg Gly Ser Glu Gly Gly Val Ala Leu Gly Ser Tyr Leu
 1               5                  10                  15

Arg Arg Leu Arg Ser Val Leu Ile Tyr Arg Thr Thr Pro Pro His His
             20                  25                  30

Thr Arg Gly Leu Pro Leu Leu Gly Leu Leu His Leu Ile Ser Leu Val
         35                  40                  45

Gly Ser Leu Leu Glu Arg Arg Ser Cys Arg Asp Pro Trp Trp Arg Gly
     50                  55                  60

Gly Lys Lys Met Ser Gly Ala Ala Leu Val Ala Ile Ala Ala Ser Ile
 65                  70                  75                  80

Gly Asn Leu Leu Gln Gly Trp Asp Asn Ala Thr Ile Ala Gly Ala Val
                 85                  90                  95

Leu Tyr Ile Lys Lys Glu Phe Gln Leu Glu Asn Asn Pro Thr Val Glu
            100                 105                 110

Gly Leu Ile Val Ala
        115

<210> SEQ ID NO 13
<211> LENGTH: 1487
<212> TYPE: DNA
<213> ORGANISM: Triticum aestivum

<400> SEQUENCE: 13
tctcttggaa agagggtggg gaggcagtca gcagcactgg tattggtggg gggtggcaac      60
tcgcatggaa atggtcggag cgacaaggcg aggatggcaa gaaggaagga ggcttcaaaa     120
gaatctactt gcaccaagag ggggtggccg actcaagaag gggctctgtt gtttcacttc     180
ctggtggggg tgatgccacg caaggggggca gtgggtttat acatgctgct gctttggtaa    240
gccactcggc tctttactcc aaggatctta tggaagagcg tatggcggcc ggtccagcca     300
tgattcatcc attggaggca gctcccaaag gttcaatctg gaaagatctg tttgaacctg     360
gtgtgaggcg tgcattgttc gtcggtgttg gaattcagat gcttcagcag tttgctggaa     420
taaatggagt tctctactat actcctcaaa ttctggagca agctggtgtg gctgttcttc     480
tttccaatct tggcctcagt tcagcatcag catccatctt gatcagttct ctcaccacct     540
tactcatgct cccaagcatt ggtgtagcca tgagacttat ggatatatct ggaagaaggt     600
ttctgctact gggcacaatt cccatcttga tagcatccct aattgttttg ggtgtggtca     660
atgttatcaa cttgagtacg gtgccccacg ctgtgctctc cacagttagc gtcattgtct     720
acttctgctg ctttgtcatg ggcttttggcc cgatccccaa cattctatgt gcagagattt     780
tccccaccag agtccgtggt gtctgcatcg ctatttgcgc cctcacattc tggatttgtg     840
acattattgt tacctacagc ctgcctgtga tgctgaatgc tattggtcta gcgggtgtct     900
ttggtatata tgcagtcgtt tgctgcattg cctttgtgtt cgtctaccta aaggtcccag     960
```

```
agacaaaggg catgcccctc gaggtcatca ccgagttctt tgcggttggg gcgaagcaag    1020
cgcaggccac cattgcctga ttcatcatgg agctttgttt tcagtttgca cactgcggtc    1080
tgcgctgaaa attgcaaatt ggacgggtcc tcgtgaggaa cggaaaaact tttgagttgt    1140
aaatgagaca gctacccaaa gagctcatca cgaggaacgg gaagctgtaa aagtaggagg    1200
atctcatgcc cccatttcat cgtctattat tgcttattag tactgtactg taatcgtcat    1260
tagttgctgt agggttgttc aacttgctaa tctgattctg aactaccatg ctgatgtccg    1320
aaataaagaa aaagcatgtt ttttttttgtg tcaacttgca aactttcttt taaacattgt    1380
gcaatgtatt gtaaatttct ttatcaactt ccctcgattc agagagaagc acttgtttgt    1440
aagtcatgaa agatttttct cgacaaaaaa aaaaaaaaaa aaaaaaa                   1487
```

```
<210> SEQ ID NO 14
<211> LENGTH: 345
<212> TYPE: PRT
<213> ORGANISM: Triticum aestivum

<400> SEQUENCE: 14

Ser Trp Lys Glu Gly Gly Glu Ala Val Ser Ser Thr Gly Ile Gly Gly
  1               5                  10                  15

Gly Trp Gln Leu Ala Trp Lys Trp Ser Glu Arg Gln Gly Glu Asp Gly
             20                  25                  30

Lys Lys Glu Gly Gly Phe Lys Arg Ile Tyr Leu His Gln Glu Gly Val
         35                  40                  45

Ala Asp Ser Arg Arg Gly Ser Val Val Ser Leu Pro Gly Gly Gly Asp
     50                  55                  60

Ala Thr Gln Gly Gly Ser Gly Phe Ile His Ala Ala Leu Val Ser
 65                  70                  75                  80

His Ser Ala Leu Tyr Ser Lys Asp Leu Met Glu Glu Arg Met Ala Ala
                 85                  90                  95

Gly Pro Ala Met Ile His Pro Leu Glu Ala Ala Pro Lys Gly Ser Ile
            100                 105                 110

Trp Lys Asp Leu Phe Glu Pro Gly Val Arg Arg Ala Leu Phe Val Gly
        115                 120                 125

Val Gly Ile Gln Met Leu Gln Gln Phe Ala Gly Ile Asn Gly Val Leu
    130                 135                 140

Tyr Tyr Thr Pro Gln Ile Leu Glu Gln Ala Gly Val Ala Val Leu Leu
145                 150                 155                 160

Ser Asn Leu Gly Leu Ser Ser Ala Ser Ala Ser Ile Leu Ile Ser Ser
                165                 170                 175

Leu Thr Thr Leu Leu Met Leu Pro Ser Ile Gly Val Ala Met Arg Leu
            180                 185                 190

Met Asp Ile Ser Gly Arg Arg Phe Leu Leu Leu Gly Thr Ile Pro Ile
        195                 200                 205

Leu Ile Ala Ser Leu Ile Val Leu Gly Val Val Asn Val Ile Asn Leu
    210                 215                 220

Ser Thr Val Pro His Ala Val Leu Ser Thr Val Ser Val Ile Val Tyr
225                 230                 235                 240

Phe Cys Cys Phe Val Met Gly Phe Gly Pro Ile Pro Asn Ile Leu Cys
                245                 250                 255

Ala Glu Ile Phe Pro Thr Arg Val Arg Gly Val Cys Ile Ala Ile Cys
            260                 265                 270

Ala Leu Thr Phe Trp Ile Cys Asp Ile Ile Val Thr Tyr Ser Leu Pro
```

-continued

```
                275                 280                 285
Val Met Leu Asn Ala Ile Gly Leu Ala Gly Val Phe Gly Ile Tyr Ala
        290                 295                 300

Val Val Cys Cys Ile Ala Phe Val Phe Val Tyr Leu Lys Val Pro Glu
305                 310                 315                 320

Thr Lys Gly Met Pro Leu Glu Val Ile Thr Glu Phe Phe Ala Val Gly
                325                 330                 335

Ala Lys Gln Ala Gln Ala Thr Ile Ala
                340                 345
```

<210> SEQ ID NO 15
<211> LENGTH: 1009
<212> TYPE: DNA
<213> ORGANISM: Triticum aestivum

<400> SEQUENCE: 15

```
tgaacctgga gtgaagcatg cactgttcgt tggcatagga ttacagatcc tgcagcagtt    60
tgcgggtatc aatggagtcc tctactacac acctcagata cttgagcaag caggtgtcgg   120
ggttcttcta tcaaacattg gactaagctc ttcctcagca tctattctta ttagtgcctt   180
gacaaccttg ctgatgcttc ccagcattgg catcgccatg agactcatgg atatgtcagg   240
aagaaggttt cttctccttt caacaatccc tgtcttgata gtagcgctag ctgtcttggt   300
tttagtgaat gttctggatg tcggaaccat ggtgcacgct gcgctctcaa cgatcagcgt   360
catcgtctat ttctgcttct tcgtcatggg gtttgggcct atcccaaata ttctctgcgc   420
ggagattttc cccacctctg tccgtggcat ctgcatagcc atctgcgcgc taaccttctg   480
gatcggcgac atcatcgtga catacactct ccccgtgatg ctcaatgcca ttggtctcgc   540
tggagtcttc ggcatatatg ccatcgtttg tgtactagcc tttgtattcg tctacatgaa   600
ggtccctgag acaaagggca tgcccctgga ggtcatcacc gagttcttct ctgtcggggc   660
aaagcagggc aaggaagcca cggactagtt gctctgatcc ggtgatccgc gtcgctggtg   720
gtaattttgt ggtgtcataa ctactactac actggttaac ctgcgatgct ttggtgaaga   780
aacttcaaag agagcagata cggaagactt tacatcgtga ggctgaattg tgtcgtcgta   840
ggccggcttt tggaagtagg atatgtactt agatcatctg ctcttttcgc tttggaactt   900
tctatttgtg ttattcagaa tttcttgccc atgtaactag tgctgttatc acaatttatg   960
tcgattatgt gtttgcctaa aaaaaaaaaa aaaaaaaaa aaaaaaaa              1009
```

<210> SEQ ID NO 16
<211> LENGTH: 228
<212> TYPE: PRT
<213> ORGANISM: Triticum aestivum

<400> SEQUENCE: 16

```
Glu Pro Gly Val Lys His Ala Leu Phe Val Gly Ile Gly Leu Gln Ile
  1               5                  10                  15

Leu Gln Gln Phe Ala Gly Ile Asn Gly Val Leu Tyr Tyr Thr Pro Gln
                 20                  25                  30

Ile Leu Glu Gln Ala Gly Val Gly Val Leu Leu Ser Asn Ile Gly Leu
             35                  40                  45

Ser Ser Ser Ala Ser Ile Leu Ile Ser Ala Thr Thr Leu Leu
         50                  55                  60

Met Leu Pro Ser Ile Gly Ile Ala Met Arg Leu Met Asp Met Ser Gly
 65                  70                  75                  80
```

-continued

```
Arg Arg Phe Leu Leu Leu Ser Thr Ile Pro Val Leu Ile Val Ala Leu
                85                  90                  95

Ala Val Leu Val Leu Val Asn Val Leu Asp Val Gly Thr Met Val His
            100                 105                 110

Ala Ala Leu Ser Thr Ile Ser Val Ile Val Tyr Phe Cys Phe Phe Val
        115                 120                 125

Met Gly Phe Gly Pro Ile Pro Asn Ile Leu Cys Ala Glu Ile Phe Pro
    130                 135                 140

Thr Ser Val Arg Gly Ile Cys Ile Ala Ile Cys Ala Leu Thr Phe Trp
145                 150                 155                 160

Ile Gly Asp Ile Ile Val Thr Tyr Thr Leu Pro Val Met Leu Asn Ala
                165                 170                 175

Ile Gly Leu Ala Gly Val Phe Gly Ile Tyr Ala Ile Val Cys Val Leu
            180                 185                 190

Ala Phe Val Phe Val Tyr Met Lys Val Pro Glu Thr Lys Gly Met Pro
        195                 200                 205

Leu Glu Val Ile Thr Glu Phe Phe Ser Val Gly Ala Lys Gln Gly Lys
    210                 215                 220

Glu Ala Thr Asp
225
```

<210> SEQ ID NO 17
<211> LENGTH: 615
<212> TYPE: DNA
<213> ORGANISM: Zea mays
<220> FEATURE:
<221> NAME/KEY: unsure
<222> LOCATION: (149)
<221> NAME/KEY: unsure
<222> LOCATION: (271)
<221> NAME/KEY: unsure
<222> LOCATION: (304)
<221> NAME/KEY: unsure
<222> LOCATION: (334)
<221> NAME/KEY: unsure
<222> LOCATION: (357)
<221> NAME/KEY: unsure
<222> LOCATION: (476)
<221> NAME/KEY: unsure
<222> LOCATION: (599)
<221> NAME/KEY: unsure
<222> LOCATION: (602)

<400> SEQUENCE: 17

```
gaaacgaact ctcttgagta ccacaaaaaa aaacattggc attctctgta gtagagcaca    60
gagcgaaccg tcaacgatgg cttccgctcc gctgccggcg ccatcgagc ccgggaagaa    120
aggcaacgtc aagttcgcct cgcctgcnc catcctcgcc tcaatgacct ccatccttct   180
cggctatgat atcggagtga tgagcggcgc gtcgttgtac atcaagaagg acctgaaaat   240
cagcgacgtg aagctggaga tcctgatggg natcctcaac gtgtactcgc tcatcggctc   300
gttncggca gggcggacgt ccgactggat cggncgccgt acaccatcgt gttcgcngcg   360
gtgatcttct tcgcgggcgc ttcctcatgg gcttcgccgt gaactactgg atgctcatgt   420
tcgggcgctt cgtggccggg atcggcgtgg gctacgcgct catgatcgca accgtntaca   480
cggccgaagt gtccccgcat cggccgcgcg cttcctgacg tcgttcccgg aggtgttcat   540
cacttcggca tcctctaggt acgtgtcaat aaggcttttc cgcttccgtt cgctggatng   600
cnctaatgtc ggcat                                                    615
```

<210> SEQ ID NO 18

```
<211> LENGTH: 167
<212> TYPE: PRT
<213> ORGANISM: Zea mays
<220> FEATURE:
<221> NAME/KEY: UNSURE
<222> LOCATION: (34)
<221> NAME/KEY: UNSURE
<222> LOCATION: (85)
<221> NAME/KEY: UNSURE
<222> LOCATION: (98)
<221> NAME/KEY: UNSURE
<222> LOCATION: (112)
<221> NAME/KEY: UNSURE
<222> LOCATION: (151)

<400> SEQUENCE: 18
```

Ser Arg Ala Gln Ser Glu Pro Ser Thr Met Ala Ser Ala Pro Leu Pro
 1               5                  10                  15

Ala Ala Ile Glu Pro Gly Lys Lys Gly Asn Val Lys Phe Ala Phe Ala
            20                  25                  30

Cys Xaa Ile Leu Ala Ser Met Thr Ser Ile Leu Leu Gly Tyr Asp Ile
        35                  40                  45

Gly Val Met Ser Gly Ala Ser Leu Tyr Ile Lys Lys Asp Leu Lys Ile
    50                  55                  60

Ser Asp Val Lys Leu Glu Ile Leu Met Gly Ile Leu Asn Val Tyr Ser
65                  70                  75                  80

Leu Ile Gly Ser Xaa Ala Ala Gly Arg Thr Ser Asp Trp Ile Gly Arg
                85                  90                  95

Arg Xaa Thr Ile Val Phe Ala Ala Val Ile Phe Phe Ala Gly Ala Xaa
        100                 105                 110

Leu Met Gly Phe Ala Val Asn Tyr Trp Met Leu Met Phe Gly Arg Phe
    115                 120                 125

Val Ala Gly Ile Gly Val Gly Tyr Ala Leu Met Ile Ala Thr Val Tyr
130                 135                 140

Thr Ala Glu Val Ser Pro Xaa Ser Ala Arg Gly Phe Leu Thr Ser Phe
145                 150                 155                 160

Pro Glu Val Phe Ile Thr Ser
                165

```
<210> SEQ ID NO 19
<211> LENGTH: 1914
<212> TYPE: DNA
<213> ORGANISM: Zea mays

<400> SEQUENCE: 19
```

| | | | | |
|---|---|---|---|---|
| gcacgaggca cgccacctta tctctaaccg gagatcaaag aagtagccgt taacgatggc | 60 |
| ttccgacgag ctcgcaaagg ccgtcgagcc caggaagaag gcaacgtca agtatgcctc | 120 |
| catatgtgcc atcctggcct ccatggcctc tgtcatcctt ggctatgaca ttggggtgat | 180 |
| gagtggagcg gccatgtaca tcaagaagga cctgaatatc acggacgtgc agctggagat | 240 |
| cctgatcggg atcctcagtc tctactcgct gttcggatcc ttcgctggcg cgcggacgtc | 300 |
| cgacaggatc gggcgccgct tgaccgtcgt gttcgccgct gtcatcttct tcgtgggctc | 360 |
| gttgctcatg ggtttcgccg tcaactacgg catgctcatg gcgggccgct tcgtggccgg | 420 |
| agtcggtgtg ggctacgggg gcatgatcgc gcccgtgtac acggccgaga tctcgcctgc | 480 |
| ggcgtcccgt ggcttcctga ccaccttccc ggaggtgttc atcaacatcg gcatcctgct | 540 |
| tggctacctg tccaacttcg cgttcgcgcg cctcccgctc cacctcggct ggcgcgtcat | 600 |
| gctcgccatt ggcgcagttc cgtccggcct gctcgcgctc ctggtgttct gcatgcccga | 660 |

-continued

```
gtcgcctcgg tggctggtct tgaagggccg cctcgcggac gccagggctg tgctagagaa    720
gacctctgcc acgccagagg aggccgccga gcggctggcc gacatcaagg ccgcggcggg    780
gattccgaag ggcctcgacg gggacgtagt caccgtaccc ggcaaggagc aaggcggcgg    840
tgagttgcag gtgtggaaga agctcatcct gtccccgacc ccggctgtcc gacgcatact    900
gctctcggcc gtgggtctcc acttcttcca gcaggcttct ggcagcgact ccgtcgtcca    960
gtacagcgcc cgcctgttca agagcgcggg gatcaccgac gacaacaagc tcctgggcgt   1020
cacctgcgcg gtgggcgtga ccaagacgtt cttcatcctg gtggccacgt cctgctgga    1080
ccgcgcgggg cgtcggcctc tgctgctgat cagcacgggc gggatgattg tctcgctcat   1140
ctgcctcggg tcgggctca ccgtcgcggg gcatcacccg acaccaagg tcgcgtgggc    1200
cgtcgccctg tgcatcgcgt caaccctgtc ctacatcgcc ttcttctcca tcggcctcgg   1260
gcccatcacg ggcgtgtaca cctcggaaat attcccgctg caggtgcgcg cgctgggctt   1320
cgcggtgggt gtggcgagca accgcgtcac cagcgccgtc atctccatga ccttcctgtc   1380
cctctccaag gccatcacca tcggcggcag cttcttcctc tactccggca tcgccgcgt   1440
cgcttgggtt ttcttcttca cgtgcctccc ggagacacgc ggccggacgc tggaggagat   1500
gggcaagctg ttcggcatgc agacacgggc atggctgaa gaagcagaag acgccgcagc    1560
caaggagaag gtggtggaac tgcctagcag caagtaggtg gctatcccag agcacaggtc   1620
aagtgaagta gatggacaag atcattgtct tttcaactaa ttagatgggc aagaataact   1680
aagactgccc tatgaggtgt cgtggttcaa ccagagatca ttctgctcct tttcttttcc   1740
cttccttttt cgagtaccat tcccattcgt cgtggtcagt acgatgttgg gtcgttggga   1800
gttagtggtg tcagagtccg cgtgtgcttt gcaagccagg gctgaaccca caatcatcag   1860
taacaaaaat tcttccgttt gctttgcaag ccaaaaaaaa aaaaaaaaaa aaaa          1914
```

<210> SEQ ID NO 20
<211> LENGTH: 513
<212> TYPE: PRT
<213> ORGANISM: Zea mays

<400> SEQUENCE: 20

```
Met Ala Ser Asp Glu Leu Ala Lys Ala Val Glu Pro Arg Lys Lys Gly
  1               5                  10                  15

Asn Val Lys Tyr Ala Ser Ile Cys Ala Ile Leu Ala Ser Met Ala Ser
             20                  25                  30

Val Ile Leu Gly Tyr Asp Ile Gly Val Met Ser Gly Ala Ala Met Tyr
         35                  40                  45

Ile Lys Lys Asp Leu Asn Ile Thr Asp Val Gln Leu Glu Ile Leu Ile
     50                  55                  60

Gly Ile Leu Ser Leu Tyr Ser Leu Phe Gly Ser Phe Ala Gly Ala Arg
 65                  70                  75                  80

Thr Ser Asp Arg Ile Gly Arg Arg Leu Thr Val Val Phe Ala Ala Val
                 85                  90                  95

Ile Phe Phe Val Gly Ser Leu Leu Met Gly Phe Ala Val Asn Tyr Gly
            100                 105                 110

Met Leu Met Ala Gly Arg Phe Val Ala Gly Val Gly Val Gly Tyr Gly
        115                 120                 125

Gly Met Ile Ala Pro Val Tyr Thr Ala Glu Ile Ser Pro Ala Ala Ser
    130                 135                 140

Arg Gly Phe Leu Thr Thr Phe Pro Glu Val Phe Ile Asn Ile Gly Ile
```

```
            145                 150                 155                 160
Leu Leu Gly Tyr Leu Ser Asn Phe Ala Phe Ala Arg Leu Pro Leu His
                165                 170                 175
Leu Gly Trp Arg Val Met Leu Ala Ile Gly Ala Val Pro Ser Gly Leu
            180                 185                 190
Leu Ala Leu Leu Val Phe Cys Met Pro Glu Ser Pro Arg Trp Leu Val
            195                 200                 205
Leu Lys Gly Arg Leu Ala Asp Ala Arg Ala Val Leu Glu Lys Thr Ser
            210                 215                 220
Ala Thr Pro Glu Glu Ala Ala Glu Arg Leu Ala Asp Ile Lys Ala Ala
225                 230                 235                 240
Ala Gly Ile Pro Lys Gly Leu Asp Gly Asp Val Val Thr Val Pro Gly
                245                 250                 255
Lys Glu Gln Gly Gly Glu Leu Gln Val Trp Lys Lys Leu Ile Leu
                260                 265                 270
Ser Pro Thr Pro Ala Val Arg Arg Ile Leu Leu Ser Ala Val Gly Leu
            275                 280                 285
His Phe Phe Gln Gln Ala Ser Gly Ser Asp Ser Val Val Gln Tyr Ser
            290                 295                 300
Ala Arg Leu Phe Lys Ser Ala Gly Ile Thr Asp Asp Asn Lys Leu Leu
305                 310                 315                 320
Gly Val Thr Cys Ala Val Gly Val Thr Lys Thr Phe Phe Ile Leu Val
                325                 330                 335
Ala Thr Phe Leu Leu Asp Arg Ala Gly Arg Arg Pro Leu Leu Leu Ile
            340                 345                 350
Ser Thr Gly Gly Met Ile Val Ser Leu Ile Cys Leu Gly Ser Gly Leu
            355                 360                 365
Thr Val Ala Gly His His Pro Asp Thr Lys Val Ala Trp Ala Val Ala
            370                 375                 380
Leu Cys Ile Ala Ser Thr Leu Ser Tyr Ile Ala Phe Phe Ser Ile Gly
385                 390                 395                 400
Leu Gly Pro Ile Thr Gly Val Tyr Thr Ser Glu Ile Phe Pro Leu Gln
                405                 410                 415
Val Arg Ala Leu Gly Phe Ala Val Gly Val Ala Ser Asn Arg Val Thr
            420                 425                 430
Ser Ala Val Ile Ser Met Thr Phe Leu Ser Leu Ser Lys Ala Ile Thr
            435                 440                 445
Ile Gly Gly Ser Phe Phe Leu Tyr Ser Gly Ile Ala Ala Val Ala Trp
            450                 455                 460
Val Phe Phe Phe Thr Cys Leu Pro Glu Thr Arg Gly Arg Thr Leu Glu
465                 470                 475                 480
Glu Met Gly Lys Leu Phe Gly Met Pro Asp Thr Gly Met Ala Glu Glu
                485                 490                 495
Ala Glu Asp Ala Ala Lys Glu Lys Val Val Glu Leu Pro Ser Ser
            500                 505                 510
Lys

<210> SEQ ID NO 21
<211> LENGTH: 2017
<212> TYPE: DNA
<213> ORGANISM: Oryza sativa

<400> SEQUENCE: 21
cttacatgta agctcgtgcc ggcacgagct tacactcgac cgccactact gtacacggcc    60
```

-continued

```
cagagcgagc ctcctcctcc tctgcaccac cggagatggc ttccgccgcg ctgccggagg      120
ccgtcgcgcc gaagaagaag ggcaacgtcc ggttcgcctt cgcctgcgcc atcctcgcct      180
ccatgacctc catcctcctc ggctacgata tcggggtgat gagcggggcg tcgctgtaca      240
tcaagaagga cttcaacatc agtgacggga aggtggaggt tctcatgggc atactgaacc      300
tctactcgct catcggctcc ttcgcggcgg gcggacgtc ggactggatc ggccggcggt       360
acaccatcgt gttcgccgcc gtcatattct tcgcgggggs gttcctcatg gggttcgccg      420
tcaactacgc catgctcatg ttcggccgct cgtggccgg catcggcgtg ggctacgcgc       480
tcatgatcgc gccggtgtac accgccgagg tgtcgccggc gtcggcgcgt ggcttcctga      540
cgtcgttccc ggaggtgttc atcaacttcg catcctgct cgggtacgtc tcgaactatg       600
ctttctcccg cttgccgctg aacctcgggt ggcgcatcat gctcggcatc ggcgcggcgc      660
cgtccgtgct gctcgcgctc atggtgctcg gcatgccgga gtcgccgcgg tggctggtca     720
tgaagggacg cctcgcggac gccaaggtgg tgctggagaa gacctccgac acggcggagg     780
aggccgcgga gcgcctggcc gacatcaagg ccgccgccgg catccctgag gagctcgacg     840
gcgacgtggt gaccgtcccc aagagaggga gcggaaacga gaagcgggtg tggaaggagc     900
tcatcctgtc cccgaccccg gccatgcggc gcatcctgct gtccgggatc ggcatccact     960
tcttccagca tgcgttgggc attcactccg tcgtcttcta cagccctctc gtgttcaaga    1020
gccccggatt aacgaacgac aaacacttct tgggcaccac ttggccgttc ggtgtcacca    1080
agaggctttt catcttgttg gcgactttct tcatcgacgg cgtcgggcgg cggccgctgt    1140
tgctgggcag cacgggcggg ataatcctct ccctcatcgg cctcggcgcc gggctcaccg    1200
tcgtcggcca gcaccccgac gccaagatac cttgggccat cggcctaagc atcgcctcca    1260
ccctcgccta cgtcgccttc ttctccatcg gccttggccc catcacgtgg gtgtacagct    1320
cggagatctt cccgctccag gtgcgcgcgc tgggctgctc gctcggcgtc gccgccaacc    1380
gcgtcaccag cggcgtcatc tccatgacct tcctgtcgct gtccaaggcc atcaccatcg    1440
gcggcagctt cttcctctac tccggcatcg ccgcgctcgc ctgggtgttc ttctacacct    1500
acctcccgga gacccgcggc cggacgctgg aggagatgag caagctgttc ggcgacacgg    1560
ccgccgcctc ggaatcagac gagccagcca aggagaagaa gaaggtggaa atggccgcca    1620
ctaactgatc aaactaaccg caaatcacc aaatcctaag ggttttcttg caaaaacgtg      1680
tgctgtactg gctagctagc aagtagtagc agcaacgtgg gaagattcgc tgatccggcg    1740
ttgctggaga gcgacggccg gcgacgacaa agctgagctc cagctcgaga cttcttaaaa    1800
tcatcttcaa gtacatggat tttatttgc tctttgcttt gtccgtaaaa gttgtactat     1860
gcgatgaaga ataccagtat gtagcaaggc tgaggttgtg tgtagctact agaagtgtca    1920
gtcacgttgt tcttgtaaga aatgtttaac tgttaattaa gcagtattgt tgcagtaatc    1980
aaaaaaaaa aaaaaaaaa aaaaaaaaa aaaaaaa                                2017
```

<210> SEQ ID NO 22
<211> LENGTH: 510
<212> TYPE: PRT
<213> ORGANISM: Oryza sativa
<220> FEATURE:
<221> NAME/KEY: UNSURE
<222> LOCATION: (102)

<400> SEQUENCE: 22

Met Ala Ser Ala Ala Leu Pro Glu Ala Val Ala Pro Lys Lys Lys Gly

-continued

```
  1               5              10              15
Asn Val Arg Phe Ala Phe Ala Cys Ala Ile Leu Ala Ser Met Thr Ser
             20                  25                  30
Ile Leu Leu Gly Tyr Asp Ile Gly Val Met Ser Gly Ala Ser Leu Tyr
             35                  40                  45
Ile Lys Lys Asp Phe Asn Ile Ser Asp Gly Lys Val Glu Val Leu Met
             50                  55                  60
Gly Ile Leu Asn Leu Tyr Ser Leu Ile Gly Ser Phe Ala Ala Gly Arg
 65                  70                  75                  80
Thr Ser Asp Trp Ile Gly Arg Arg Tyr Thr Ile Val Phe Ala Ala Val
                 85                  90                  95
Ile Phe Phe Ala Gly Xaa Phe Leu Met Gly Phe Ala Val Asn Tyr Ala
                100                 105                 110
Met Leu Met Phe Gly Arg Phe Val Ala Gly Ile Gly Val Gly Tyr Ala
                115                 120                 125
Leu Met Ile Ala Pro Val Tyr Thr Ala Glu Val Ser Pro Ala Ser Ala
                130                 135                 140
Arg Gly Phe Leu Thr Ser Phe Pro Glu Val Phe Ile Asn Phe Gly Ile
145                 150                 155                 160
Leu Leu Gly Tyr Val Ser Asn Tyr Ala Phe Ser Arg Leu Pro Leu Asn
                165                 170                 175
Leu Gly Trp Arg Ile Met Leu Gly Ile Gly Ala Ala Pro Ser Val Leu
                180                 185                 190
Leu Ala Leu Met Val Leu Gly Met Pro Glu Ser Pro Arg Trp Leu Val
                195                 200                 205
Met Lys Gly Arg Leu Ala Asp Ala Lys Val Val Leu Glu Lys Thr Ser
                210                 215                 220
Asp Thr Ala Glu Glu Ala Ala Glu Arg Leu Ala Asp Ile Lys Ala Ala
225                 230                 235                 240
Ala Gly Ile Pro Glu Glu Leu Asp Gly Asp Val Val Thr Val Pro Lys
                245                 250                 255
Arg Gly Ser Gly Asn Glu Lys Arg Val Trp Lys Glu Leu Ile Leu Ser
                260                 265                 270
Pro Thr Pro Ala Met Arg Arg Ile Leu Leu Ser Gly Ile Gly Ile His
                275                 280                 285
Phe Phe Gln His Ala Leu Gly Ile His Ser Val Val Phe Tyr Ser Pro
                290                 295                 300
Leu Val Phe Lys Ser Pro Gly Leu Thr Asn Asp Lys His Phe Leu Gly
305                 310                 315                 320
Thr Thr Trp Pro Phe Gly Val Thr Lys Arg Leu Phe Ile Leu Leu Ala
                325                 330                 335
Thr Phe Phe Ile Asp Gly Val Gly Arg Arg Pro Leu Leu Leu Gly Ser
                340                 345                 350
Thr Gly Gly Ile Ile Leu Ser Leu Ile Gly Leu Gly Ala Gly Leu Thr
                355                 360                 365
Val Val Gly Gln His Pro Asp Ala Lys Ile Pro Trp Ala Ile Gly Leu
                370                 375                 380
Ser Ile Ala Ser Thr Leu Ala Tyr Val Ala Phe Phe Ser Ile Gly Leu
385                 390                 395                 400
Gly Pro Ile Thr Trp Val Tyr Ser Ser Glu Ile Phe Pro Leu Gln Val
                405                 410                 415
Arg Ala Leu Gly Cys Ser Leu Gly Val Ala Ala Asn Arg Val Thr Ser
                420                 425                 430
```

```
Gly Val Ile Ser Met Thr Phe Leu Ser Leu Ser Lys Ala Ile Thr Ile
            435                 440                 445

Gly Gly Ser Phe Phe Leu Tyr Ser Gly Ile Ala Ala Leu Ala Trp Val
        450                 455                 460

Phe Phe Tyr Thr Tyr Leu Pro Glu Thr Arg Gly Arg Thr Leu Glu Glu
465                 470                 475                 480

Met Ser Lys Leu Phe Gly Asp Thr Ala Ala Ser Glu Ser Asp Glu
                485                 490                 495

Pro Ala Lys Glu Lys Lys Val Glu Met Ala Ala Thr Asn
            500                 505                 510

<210> SEQ ID NO 23
<211> LENGTH: 1853
<212> TYPE: DNA
<213> ORGANISM: Glycine max

<400> SEQUENCE: 23
```

| | | | | | |
|---|---|---|---|---|---|
| gcacgagagt | ttctctcttc | acatatcatc | atacttagat | agtcagatac | atcacccaat | 60 |
| aattaaatta | aatacatgct | agcactttaa | cagtactcct | ttctctaata | tctctctcat | 120 |
| attttccttt | ctgcggatat | tcagctaatt | aaactaagtc | actaagatga | ctgagggaaa | 180 |
| gctagttgaa | gctgcagaag | ctcataagac | acttcaggat | ttcgatcctc | caaagaagcg | 240 |
| caaaaggaac | aagtatgctt | tgcttgtgc | tatgctggcc | tccatgactt | ccatcttgct | 300 |
| tggttatgat | attggagtga | tgagtggagc | agccatatac | ataaaaaggg | acctgaaagt | 360 |
| ctcggacgag | caaatcgaga | tcctgctcgg | aatcatcaac | ctatactctc | tgataggctc | 420 |
| atgtctcgcc | ggcagaacct | ccgactggat | aggtccccgt | tacacgattg | ttttcgccgg | 480 |
| caccatcttc | tttgtcggag | cacttctcat | gggtttctcc | cccaattatt | cctttctcat | 540 |
| gtttggccgt | ttcgtcgctg | gcattggcat | cggctacgcc | ctcatgatag | ccccgtcta | 600 |
| caccgccgag | gtctccccgg | cctcctctcg | tggcttcctc | acttccttcc | ctgaggtatt | 660 |
| tattaatgga | gggatattaa | ttggatacat | atcaaactat | gcattttcga | agctgacact | 720 |
| aaaggtggga | tggcgaatga | tgcttggagt | tggtgcaata | ccttcggtac | tcctaacagt | 780 |
| aggagtgttg | gcgatgccgg | agtccccaag | gtggcttgtg | atgaggggtc | gtttgggaga | 840 |
| ggcaagaaaa | gtgcttaaca | aaacctcaga | cagcaaggaa | gaggcccaac | taaggctagc | 900 |
| ggaaatcaaa | caagccgcag | ggatccccga | gagttcaac | gacgacgtcg | ttcaggtaaa | 960 |
| taaacaaagc | aacggtgaag | gtgtatggaa | agagctcttc | ctctatccaa | cgcccgcaat | 1020 |
| tcgtcacatc | gtaatcgctg | cccttggtat | tcacttcttc | caacaagcgt | cgggcgtaga | 1080 |
| cgccgtcgtt | ttgtacagcc | ccaggatctt | cgaaaaggct | gggattacaa | acgacacgca | 1140 |
| taagcttctt | gcaaccgtgg | ccgttggatt | cgttaagacc | gtgttcatct | tggcggctac | 1200 |
| gtttacgttg | gaccgcgtgg | gtcgtcgtcc | gttgttattg | tctagtgtcg | gcggcatggt | 1260 |
| gctctcgctt | ctcacgcttg | cgatcagcct | cactgttatt | gatcattcgg | agaggaaatt | 1320 |
| aatgtgggcc | gttggatcga | gcatagccat | ggtgttggct | tacgtggcca | cgttctccat | 1380 |
| cggtgcgggt | cccatcacgt | gggtctatag | ttctgagatc | ttcccgttga | ggctgcgggc | 1440 |
| gcarggtgcg | gccgcgggag | ttgcggtgaa | taggaccact | agcgcggttg | tctcaatgac | 1500 |
| ttttctgtcc | ctcactagag | ccatcactat | tggtggagct | ttcttccttt | attgtggcat | 1560 |
| tgctactgtt | gggtggatat | tcttttacac | cgtcttgcct | gagacccggg | gaaaacgct | 1620 |
| cgaagacatg | gaagggtctt | tggtactttt | taggtccaaa | tccaacgcca | gcaaggctgt | 1680 |

-continued

```
agaaaatgag aatgggcaag tagcacaagt ccagctagga accaatgtcc aaacttgaaa      1740
aatgagtatt gggacatcca gtaatagtga agtaatttcg tgattttttt tttgtttttt      1800 acttttaga ctagttcttc aaatcaaaac gagaagttaa agtgaaaaaa aaa              1853
```

<210> SEQ ID NO 24
<211> LENGTH: 523
<212> TYPE: PRT
<213> ORGANISM: Glycine max

<400> SEQUENCE: 24

```
Met Thr Glu Gly Lys Leu Val Glu Ala Ala Ala His Lys Thr Leu
 1               5                  10                  15

Gln Asp Phe Asp Pro Lys Lys Arg Lys Arg Asn Lys Tyr Ala Phe
            20                  25                  30

Ala Cys Ala Met Leu Ala Ser Met Thr Ser Ile Leu Leu Gly Tyr Asp
         35                  40                  45

Ile Gly Val Met Ser Gly Ala Ala Ile Tyr Ile Lys Arg Asp Leu Lys
     50                  55                  60

Val Ser Asp Glu Gln Ile Glu Ile Leu Gly Ile Ile Asn Leu Tyr
 65                  70                  75                  80

Ser Leu Ile Gly Ser Cys Leu Ala Gly Arg Thr Ser Asp Trp Ile Gly
                 85                  90                  95

Pro Arg Tyr Thr Ile Val Phe Ala Gly Thr Ile Phe Val Gly Ala
            100                 105                 110

Leu Leu Met Gly Phe Ser Pro Asn Tyr Ser Phe Leu Met Phe Gly Arg
        115                 120                 125

Phe Val Ala Gly Ile Gly Ile Gly Tyr Ala Leu Met Ile Ala Pro Val
    130                 135                 140

Tyr Thr Ala Glu Val Ser Pro Ala Ser Ser Arg Gly Phe Leu Thr Ser
145                 150                 155                 160

Phe Pro Glu Val Phe Ile Asn Gly Gly Ile Leu Ile Gly Tyr Ile Ser
                165                 170                 175

Asn Tyr Ala Phe Ser Lys Leu Thr Leu Lys Val Gly Trp Arg Met Met
            180                 185                 190

Leu Gly Val Gly Ala Ile Pro Ser Val Leu Leu Thr Val Gly Val Leu
        195                 200                 205

Ala Met Pro Glu Ser Pro Arg Trp Leu Val Met Arg Gly Arg Leu Gly
    210                 215                 220

Glu Ala Arg Lys Val Leu Asn Lys Thr Ser Asp Ser Lys Glu Glu Ala
225                 230                 235                 240

Gln Leu Arg Leu Ala Glu Ile Lys Gln Ala Gly Ile Pro Glu Ser
                245                 250                 255

Cys Asn Asp Asp Val Val Gln Val Asn Lys Gln Ser Asn Gly Glu Gly
            260                 265                 270

Val Trp Lys Glu Leu Phe Leu Tyr Pro Thr Pro Ala Ile Arg His Ile
        275                 280                 285

Val Ile Ala Ala Leu Gly Ile His Phe Phe Gln Gln Ala Ser Gly Val
    290                 295                 300

Asp Ala Val Val Leu Tyr Ser Pro Arg Ile Phe Glu Lys Ala Gly Ile
305                 310                 315                 320

Thr Asn Asp Thr His Lys Leu Leu Ala Thr Val Ala Val Gly Phe Val
                325                 330                 335

Lys Thr Val Phe Ile Leu Ala Ala Thr Phe Thr Leu Asp Arg Val Gly
```

```
                340             345             350
Arg Arg Pro Leu Leu Ser Ser Val Gly Gly Met Val Leu Ser Leu
        355                 360                 365
Leu Thr Leu Ala Ile Ser Leu Thr Val Ile Asp His Ser Glu Arg Lys
    370                 375                 380
Leu Met Trp Ala Val Gly Ser Ser Ile Ala Met Val Leu Ala Tyr Val
385                 390                 395                 400
Ala Thr Phe Ser Ile Gly Ala Gly Pro Ile Thr Trp Val Tyr Ser Ser
                405                 410                 415
Glu Ile Phe Pro Leu Arg Leu Arg Ala Gln Gly Ala Ala Ala Gly Val
                420                 425                 430
Ala Val Asn Arg Thr Thr Ser Ala Val Val Ser Met Thr Phe Leu Ser
                435                 440                 445
Leu Thr Arg Ala Ile Thr Ile Gly Gly Ala Phe Phe Leu Tyr Cys Gly
    450                 455                 460
Ile Ala Thr Val Gly Trp Ile Phe Phe Tyr Thr Val Leu Pro Glu Thr
465                 470                 475                 480
Arg Gly Lys Thr Leu Glu Asp Met Glu Gly Ser Phe Gly Thr Phe Arg
                485                 490                 495
Ser Lys Ser Asn Ala Ser Lys Ala Val Glu Asn Glu Asn Gly Gln Val
                500                 505                 510
Ala Gln Val Gln Leu Gly Thr Asn Val Gln Thr
                515                 520

<210> SEQ ID NO 25
<211> LENGTH: 2089
<212> TYPE: DNA
<213> ORGANISM: Triticum aestivum

<400> SEQUENCE: 25
agcaccacta aactatacac aaggaggacc tcgtcggcat aatcctcagg cagcgagcag      60
aggggcgtcg tcgacgatgg accgcgccgc actcccggcg gccgtcgagc caagaagaa     120
gggcaacgtg aggttcgcct tcgcctgcgc catcctcgcc tccatgacct ccatcctcct     180
cggctacgac atcggcgtga tgagcggagc gtcgctgtac atccagaagg atctgaagat     240
caacgacacc cagctggagg tcctcatggg catcctcaac gtgtactcgc tcattggctc     300
cttcgcggcg gggcggacgt ccgactggat cggccggcgc ttcaccatcg tcttcgccgc     360
cgtcatcttc ttcgcgggcg ccctcatcat gggcttctcc gtcaactacg ccatgctcat     420
gttcgggcgc ttcgtggccg gcatcggcgt ggggtacgct ctcatgatcg cgcccgtgaa     480
cacgggcgag gtgtcccccg cgtctgcccg tggggttctc acatccttcc ggaggtgtt     540
catcaacttc ggcatcctcc tcggatatgt ctccaacttc gccttcgccc gcctctccct     600
ccgcctcggc tggcgcatta tgctcggcat aggcgcggtg ccgtccgtcc tgctcgcgtt     660
catggtgctc ggcatgcccg agtctccccg gtggctcgtc atgaagggcc gtctcgcgga     720
cgccaaggtt gtgcttgcca agacgtccga cacgccggaa gaggccgccg agcgcatcgc     780
cgacattaag actccgccg gcatccctct gggcctcgac ggcgacgtgg tccccgtgcc     840
caaaaacaaa ggaagcagcg aggagaagcg cgttttgaag gacctcatcc tgtcaccgac     900
catagccatg cgccacatcc tcatcgcggg aatcggcatc cacttcttcc agcagtcttc     960
gggcatcgac gccgtcgtgc tctacagccc gctagttttc aagagcgccg gcatcacggg    1020
cgacagccgt ctccgcggca ccaccgtggc ggtcggggcc accaatacgg tcttcatcct    1080
```

```
ggtggccacc ttcctcctcg accgcatccg ccggcggccg ctggtgctga ccagcacggg    1140
cggcatgctc gtctccttag tgggcctcgc gacgggctc  accgtcatca gccgccaccc    1200
ggacgagaag atcacctggg ccatcgtcct gtgcatcttc tgcatcatgg cctacgtggc    1260
cttcttctcc atcggcctcg gccccatcac gtgggtgtac agctcggaga tcttcccgct    1320
gcacgtgcgc gcgctgggct gctccctggg cgtggccgtc aaccgcctga ccagcggcgt    1380
gatctccatg accttcattt cgctgtccaa ggccatgacc atcggcggcg ccttcttcct    1440
cttcgccggc atcgcctcat tcgcatgggt gttcttcttc gcctacctgc ggagacccg    1500 cggccgcacg ctggaggaca tgagctcgct gttcggcaac acggccacgc acaagcaggg    1560
cgccgcggaa gccgacgacg acgccgggga agaaggtg  gaaatggccg ccaccaactg    1620
accgcaagtt ggcagatcgc gatgcgaaga cttgcgctgt atccgtctcg gctagctagc    1680
tgccacaagg ccacatagat gacgaagtag cgtgggaaga ttcgctgatc cggccggagc    1740
tgccggaggg cgacggcaag ctccagctcg atcgagacgt taatggcttc ttaaatgtgc    1800
taagtttaat gtttcgctct ttggttttgt ccgggtaggt cgtgagcaat ccggtagtgc    1860
cgatgccaag gctaatcgac gccggacgga ctagactact gtagtagact gtagaggtgt    1920
accgttgcta cttccgtggc gtttgtctgc atgattagga gagaaactg  gcggtggttc    1980 gaggactcta cctgccgatc gagtgagtca agcgagccac ggaaaatgtg taagaaaaaa    2040
atattaagta tgtgtattgt aaaaaaaaaa aaaaaaaaa  aaaaaaaaa               2089
```

<210> SEQ ID NO 26
<211> LENGTH: 539
<212> TYPE: PRT
<213> ORGANISM: Triticum aestivum

<400> SEQUENCE: 26

```
Ala Pro Leu Asn Tyr Thr Gln Gly Gly Pro Arg Arg His Asn Pro Gln
 1               5                   10                  15

Ala Ala Ser Arg Gly Ala Ser Ser Thr Met Asp Arg Ala Ala Leu Pro
             20                  25                  30

Ala Ala Val Glu Pro Lys Lys Lys Gly Asn Val Arg Phe Ala Phe Ala
         35                  40                  45

Cys Ala Ile Leu Ala Ser Met Thr Ser Ile Leu Leu Gly Tyr Asp Ile
     50                  55                  60

Gly Val Met Ser Gly Ala Ser Leu Tyr Ile Gln Lys Asp Leu Lys Ile
 65                  70                  75                  80

Asn Asp Thr Gln Leu Glu Val Leu Met Gly Ile Leu Asn Val Tyr Ser
                 85                  90                  95

Leu Ile Gly Ser Phe Ala Ala Gly Arg Thr Ser Asp Trp Ile Gly Arg
            100                 105                 110

Arg Phe Thr Ile Val Phe Ala Ala Val Ile Phe Phe Ala Gly Ala Leu
        115                 120                 125

Ile Met Gly Phe Ser Val Asn Tyr Ala Met Leu Met Phe Gly Arg Phe
    130                 135                 140

Val Ala Gly Ile Gly Val Gly Tyr Ala Leu Met Ile Ala Pro Val Asn
145                 150                 155                 160

Thr Gly Glu Val Ser Pro Ala Ser Ala Arg Gly Val Leu Thr Ser Phe
                165                 170                 175

Pro Glu Val Phe Ile Asn Phe Gly Ile Leu Leu Gly Tyr Val Ser Asn
            180                 185                 190

Phe Ala Phe Ala Arg Leu Ser Leu Arg Leu Gly Trp Arg Ile Met Leu
```

```
                195                 200                 205
Gly Ile Gly Ala Val Pro Ser Val Leu Leu Ala Phe Met Val Leu Gly
        210                 215                 220

Met Pro Glu Ser Pro Arg Trp Leu Val Met Lys Gly Arg Leu Ala Asp
225                 230                 235                 240

Ala Lys Val Val Leu Ala Lys Thr Ser Asp Thr Pro Glu Glu Ala Ala
                245                 250                 255

Glu Arg Ile Ala Asp Ile Lys Thr Ala Ala Gly Ile Pro Leu Gly Leu
                260                 265                 270

Asp Gly Asp Val Val Pro Val Pro Lys Asn Lys Gly Ser Ser Glu Glu
            275                 280                 285

Lys Arg Val Leu Lys Asp Leu Ile Leu Ser Pro Thr Ile Ala Met Arg
290                 295                 300

His Ile Leu Ile Ala Gly Ile Gly Ile His Phe Phe Gln Gln Ser Ser
305                 310                 315                 320

Gly Ile Asp Ala Val Val Leu Tyr Ser Pro Leu Val Phe Lys Ser Ala
                325                 330                 335

Gly Ile Thr Gly Asp Ser Arg Leu Arg Gly Thr Thr Val Ala Val Gly
                340                 345                 350

Ala Thr Asn Thr Val Phe Ile Leu Val Ala Thr Phe Leu Leu Asp Arg
                355                 360                 365

Ile Arg Arg Arg Pro Leu Val Leu Thr Ser Thr Gly Gly Met Leu Val
            370                 375                 380

Ser Leu Val Gly Leu Ala Thr Gly Leu Thr Val Ile Ser Arg His Pro
385                 390                 395                 400

Asp Glu Lys Ile Thr Trp Ala Ile Val Leu Cys Ile Phe Cys Ile Met
                405                 410                 415

Ala Tyr Val Ala Phe Phe Ser Ile Gly Leu Gly Pro Ile Thr Trp Val
                420                 425                 430

Tyr Ser Ser Glu Ile Phe Pro Leu His Val Arg Ala Leu Gly Cys Ser
            435                 440                 445

Leu Gly Val Ala Val Asn Arg Leu Thr Ser Gly Val Ile Ser Met Thr
450                 455                 460

Phe Ile Ser Leu Ser Lys Ala Met Thr Ile Gly Gly Ala Phe Phe Leu
465                 470                 475                 480

Phe Ala Gly Ile Ala Ser Phe Ala Trp Val Phe Phe Ala Tyr Leu
                485                 490                 495

Pro Glu Thr Arg Gly Arg Thr Leu Glu Asp Met Ser Ser Leu Phe Gly
            500                 505                 510

Asn Thr Ala Thr His Lys Gln Gly Ala Ala Glu Ala Asp Asp Asp Ala
            515                 520                 525

Gly Glu Lys Lys Val Glu Met Ala Ala Thr Asn
530                 535

<210> SEQ ID NO 27
<211> LENGTH: 1872
<212> TYPE: DNA
<213> ORGANISM: Triticum aestivum

<400> SEQUENCE: 27
gcacgagctc atcactaggc tgtcagtctg tctgttcaac gaacgatcag ttcgtcctaa    60
gcagatgaaa atgtctccgg aaagaaaagg agcggaggac aaggaagaag gatcgaggat   120
ggcttctgct gcgctcccgg agccgggggc agtccatcca aggaacaagg gcaatttcaa   180
```

-continued

```
gtacgccttc acctgcgccc tctgtgcttc catggccacc atcgtcctcg gctacgacgt    240
tggggtgatg agcggtgcgt cgctgtacat caagagggac ctgcagatca cggacgtgca    300
gctggagatc atgatgggca tcctgagcgt gtacgcgctc atcgggtcct tcctcggcgc    360
gaggacgtcc gactgggtcg gccgccgcgt caccgtcgtc ttcgcggccg ccatcttcaa    420
caacggctcc ttgctcatgg gcttcgcggt caactacgcc atgctcatgg tcgggcgctt    480
cgtcaccgga atcggcgtgg gctacgccat catggtcgcg ccagtgtaca cgcccgaggt    540
gtccccggcg tcggcccgcg gcttcctcac gtctttcacc gaggtgttca tcaatgtggg    600
catcctcctt ggctacgtct ccaactacgc cttcgcgcgc ctcccgctcc acctcagctg    660
gcgcgtcatg ctcggcatcg gcgccgtccc gtccgccctg cttgcgctca tggtgttcgg    720
catgccggag tctcctcgct ggctcgtcat gaaaggccgc ctcgcggacg ccagggccgt    780
tctggccaag acctccgaca cgccggagga ggccgtggag cgccttgacc agatcaaggc    840
tgccgccggc atccctaggg aacttgacgg cgacgtggtc gtcatgccta agacaaaagg    900
cggccaggag aagcaggtgt ggaaggagct catcttttcg ccgaccccag ccatgcggcg    960
catactgctc gcggcgctcg gcatccattt ctttcagcag gcgacgggct ccgactccgt   1020
cgtgctctat agcccacgcg tgttccagag cgcgggcatc accggcgaca accacctgct   1080
cggcgccaca tgcgccatgg gggtcatgaa gacgctcttc atcctggtgg ccacgttcca   1140
gctcgaccgc gtcggcaggc ggccgctgct gctgaccagc acggccggca tgctcgcctg   1200
tctcatcggc ctcgggacgg gcctcaccgt cgtgggtcgg cacccggacg ccaaggtccc   1260
gtgggccatc ggcctgtgca tcgtgtccat cttggcctac gtgtccttct ctccatcgg    1320 cctcgggccc ctcaccagcg tgtacacctc ggaggtcttc ccactgcggg tgcgcgcgct   1380
gggcttcgcg ctgggcacgt catgcaaccg cgtcaccagc gccgcggtct ccatgtcctt   1440
cctgtccttg tccaaggcca tcaccatcgg cggcagcttc ttcctgtacg ccggcatcgc   1500
ggcgatagga tggattttct tcttcacctt cattccggag acgcgtggcc tgccgctcga   1560
ggagataggg aagcttttcg gcatgacgga cacggccgtc gaagcccaag acaccgccac   1620
gaaagacaag gcgaaagtag gggagatgaa ctagtgagct agacgtcaac caactgttac   1680
cgatgtacta ccatagagat gtatctgatc aacgtggcaa tataagtgtc acggactctt   1740
ggtgctcatt gatggattgt ttggataaaa tttcaagaga attgtttcaa gtttggatcc   1800
aaaaaaaaaa aaaaaaaaaa aaaaaaaaaa aaaaaaaaaa aaaaaaaaaa aaaaaaaaaa   1860
aaaaaaaaaa aa                                                        1872
```

<210> SEQ ID NO 28
<211> LENGTH: 529
<212> TYPE: PRT
<213> ORGANISM: Triticum aestivum

<400> SEQUENCE: 28

```
Met Lys Met Ser Pro Glu Arg Lys Gly Ala Glu Asp Lys Glu Glu Gly
  1               5                  10                  15

Ser Arg Met Ala Ser Ala Ala Leu Pro Glu Pro Gly Ala Val His Pro
             20                  25                  30

Arg Asn Lys Gly Asn Phe Lys Tyr Ala Phe Thr Cys Ala Leu Cys Ala
         35                  40                  45

Ser Met Ala Thr Ile Val Leu Gly Tyr Asp Val Gly Val Met Ser Gly
     50                  55                  60

Ala Ser Leu Tyr Ile Lys Arg Asp Leu Gln Ile Thr Asp Val Gln Leu
```

```
               65                  70                  75                  80
          Glu Ile Met Met Gly Ile Leu Ser Val Tyr Ala Leu Ile Gly Ser Phe
                               85                  90                  95
          Leu Gly Ala Arg Thr Ser Asp Trp Val Gly Arg Val Thr Val Val
                          100                 105                 110
          Phe Ala Ala Ile Phe Asn Asn Gly Ser Leu Leu Met Gly Phe Ala
                          115                 120                 125
          Val Asn Tyr Ala Met Leu Met Val Gly Arg Phe Val Thr Gly Ile Gly
                          130                 135                 140
          Val Gly Tyr Ala Ile Met Val Ala Pro Val Tyr Thr Pro Glu Val Ser
          145                 150                 155                 160
          Pro Ala Ser Ala Arg Gly Phe Leu Thr Ser Phe Thr Glu Val Phe Ile
                               165                 170                 175
          Asn Val Gly Ile Leu Leu Gly Tyr Val Ser Asn Tyr Ala Phe Ala Arg
                               180                 185                 190
          Leu Pro Leu His Leu Ser Trp Arg Val Met Leu Gly Ile Gly Ala Val
                          195                 200                 205
          Pro Ser Ala Leu Leu Ala Leu Met Val Phe Gly Met Pro Glu Ser Pro
                          210                 215                 220
          Arg Trp Leu Val Met Lys Gly Arg Leu Ala Asp Ala Arg Ala Val Leu
          225                 230                 235                 240
          Ala Lys Thr Ser Asp Thr Pro Glu Glu Ala Val Glu Arg Leu Asp Gln
                               245                 250                 255
          Ile Lys Ala Ala Ala Gly Ile Pro Arg Glu Leu Asp Gly Asp Val Val
                          260                 265                 270
          Val Met Pro Lys Thr Lys Gly Gly Gln Glu Lys Gln Val Trp Lys Glu
                          275                 280                 285
          Leu Ile Phe Ser Pro Thr Pro Ala Met Arg Arg Ile Leu Leu Ala Ala
                          290                 295                 300
          Leu Gly Ile His Phe Phe Gln Gln Ala Thr Gly Ser Asp Ser Val Val
          305                 310                 315                 320
          Leu Tyr Ser Pro Arg Val Phe Gln Ser Ala Gly Ile Thr Gly Asp Asn
                               325                 330                 335
          His Leu Leu Gly Ala Thr Cys Ala Met Gly Val Met Lys Thr Leu Phe
                               340                 345                 350
          Ile Leu Val Ala Thr Phe Gln Leu Asp Arg Val Gly Arg Arg Pro Leu
                          355                 360                 365
          Leu Leu Thr Ser Thr Ala Gly Met Leu Ala Cys Leu Ile Gly Leu Gly
                          370                 375                 380
          Thr Gly Leu Thr Val Val Gly Arg His Pro Asp Ala Lys Val Pro Trp
          385                 390                 395                 400
          Ala Ile Gly Leu Cys Ile Val Ser Ile Leu Ala Tyr Val Ser Phe Phe
                               405                 410                 415
          Ser Ile Gly Leu Gly Pro Leu Thr Ser Val Tyr Thr Ser Glu Val Phe
                               420                 425                 430
          Pro Leu Arg Val Arg Ala Leu Gly Phe Ala Leu Gly Thr Ser Cys Asn
                          435                 440                 445
          Arg Val Thr Ser Ala Ala Val Ser Met Ser Phe Leu Ser Leu Ser Lys
                          450                 455                 460
          Ala Ile Thr Ile Gly Gly Ser Phe Phe Leu Tyr Ala Gly Ile Ala Ala
          465                 470                 475                 480
          Ile Gly Trp Ile Phe Phe Phe Thr Phe Ile Pro Glu Thr Arg Gly Leu
                               485                 490                 495
```

```
Pro Leu Glu Glu Ile Gly Lys Leu Phe Gly Met Thr Asp Thr Ala Val
            500                 505                 510
Glu Ala Gln Asp Thr Ala Thr Lys Asp Lys Ala Lys Val Gly Glu Met
        515                 520                 525
Asn

<210> SEQ ID NO 29
<211> LENGTH: 729
<212> TYPE: PRT
<213> ORGANISM: Arabidopsis thaliana

<400> SEQUENCE: 29

Met Ser Gly Ala Val Leu Val Ala Ile Ala Ala Val Gly Asn Leu
 1               5                  10                  15

Leu Gln Gly Trp Asp Asn Ala Thr Ile Ala Gly Ala Val Leu Tyr Ile
                20                  25                  30

Lys Lys Glu Phe Asn Leu Glu Ser Asn Pro Ser Val Glu Gly Leu Ile
            35                  40                  45

Val Ala Met Ser Leu Ile Gly Ala Thr Leu Ile Thr Thr Cys Ser Gly
         50                  55                  60

Gly Val Ala Asp Trp Leu Gly Arg Arg Pro Met Leu Ile Leu Ser Ser
 65                  70                  75                  80

Ile Leu Tyr Phe Val Gly Ser Leu Val Met Leu Trp Ser Pro Asn Val
                 85                  90                  95

Tyr Val Leu Leu Leu Gly Arg Leu Leu Asp Gly Phe Gly Val Gly Leu
                100                 105                 110

Val Val Thr Leu Val Pro Ile Tyr Ile Ser Glu Thr Ala Pro Pro Glu
            115                 120                 125

Ile Arg Gly Leu Leu Asn Thr Leu Pro Gln Phe Thr Gly Ser Gly Gly
        130                 135                 140

Met Phe Leu Ser Tyr Cys Met Val Phe Gly Met Ser Leu Met Pro Ser
145                 150                 155                 160

Pro Ser Trp Arg Leu Met Leu Gly Val Leu Phe Ile Pro Ser Leu Val
                165                 170                 175

Phe Phe Phe Leu Thr Val Phe Phe Leu Pro Glu Ser Pro Arg Trp Leu
                180                 185                 190

Val Ser Lys Gly Arg Met Leu Glu Ala Lys Arg Val Leu Gln Arg Leu
            195                 200                 205

Arg Gly Arg Glu Asp Val Ser Gly Glu Met Ala Leu Leu Val Glu Gly
        210                 215                 220

Leu Gly Ile Gly Gly Glu Thr Thr Ile Glu Glu Tyr Ile Ile Gly Pro
225                 230                 235                 240

Ala Asp Glu Val Thr Asp Asp His Asp Ile Ala Val Asp Lys Asp Gln
                245                 250                 255

Ile Lys Leu Tyr Gly Ala Glu Gly Leu Ser Trp Val Ala Arg Pro
            260                 265                 270

Val Lys Gly Gly Ser Thr Met Ser Val Leu Ser Arg His Gly Ser Thr
        275                 280                 285

Met Ser Arg Arg Gln Gly Ser Leu Ile Asp Pro Leu Val Thr Leu Phe
    290                 295                 300

Gly Ser Val His Glu Lys Met Pro Asp Thr Gly Ser Met Arg Ser Ala
305                 310                 315                 320

Leu Phe Pro His Phe Gly Ser Met Phe Ser Val Gly Gly Asn Gln Pro
                325                 330                 335
```

-continued

```
Arg His Glu Asp Trp Asp Glu Asn Leu Val Gly Glu Gly Glu Asp
            340                 345                 350
Tyr Pro Ser Asp His Gly Asp Ser Glu Asp Leu His Ser Pro
        355                 360                 365
Leu Ile Ser Arg Gln Thr Thr Ser Met Glu Lys Asp Met Pro His Thr
        370                 375                 380
Ala His Gly Thr Leu Ser Thr Phe Arg His Gly Ser Gln Val Gln Gly
385                 390                 395                 400
Ala Gln Gly Glu Gly Ala Gly Ser Met Gly Ile Gly Gly Trp Gln
                405                 410                 415
Val Ala Trp Lys Trp Thr Glu Arg Glu Asp Glu Ser Gly Gln Lys Glu
                420                 425                 430
Glu Gly Phe Pro Gly Ser Arg Arg Gly Ser Ile Val Ser Leu Pro Gly
            435                 440                 445
Gly Asp Gly Thr Gly Glu Ala Asp Phe Val Gln Ala Ser Ala Leu Val
        450                 455                 460
Ser Gln Pro Ala Leu Tyr Ser Lys Asp Leu Leu Lys Glu His Thr Ile
465                 470                 475                 480
Gly Pro Ala Met Val His Pro Ser Glu Thr Thr Lys Gly Ser Ile Trp
                485                 490                 495
His Asp Leu His Asp Pro Gly Val Lys Arg Ala Leu Val Val Gly Val
                500                 505                 510
Gly Leu Gln Ile Leu Gln Gln Phe Ser Gly Ile Asn Gly Val Leu Tyr
            515                 520                 525
Tyr Thr Pro Gln Ile Leu Glu Gln Ala Gly Val Gly Ile Leu Leu Ser
        530                 535                 540
Asn Met Gly Ile Ser Ser Ser Ala Ser Leu Leu Ile Ser Ala Leu
545                 550                 555                 560
Thr Thr Phe Val Met Leu Pro Ala Ile Ala Val Ala Met Arg Leu Met
                565                 570                 575
Asp Leu Ser Gly Arg Arg Thr Leu Leu Leu Thr Thr Ile Pro Ile Leu
            580                 585                 590
Ile Ala Ser Leu Leu Val Leu Val Ile Ser Asn Leu Val His Met Asn
        595                 600                 605
Ser Ile Val His Ala Val Leu Ser Thr Val Ser Val Leu Tyr Phe
        610                 615                 620
Cys Phe Phe Val Met Gly Phe Gly Pro Ala Pro Asn Ile Leu Cys Ser
625                 630                 635                 640
Glu Ile Phe Pro Thr Arg Val Arg Gly Ile Cys Ile Ala Ile Cys Ala
                645                 650                 655
Leu Thr Phe Trp Ile Cys Asp Ile Ile Val Thr Tyr Ser Leu Pro Val
            660                 665                 670
Leu Leu Lys Ser Ile Gly Leu Ala Gly Val Phe Gly Met Tyr Ala Ile
            675                 680                 685
Val Cys Cys Ile Ser Trp Val Phe Val Phe Ile Lys Val Pro Glu Thr
        690                 695                 700
Lys Gly Met Pro Leu Glu Val Ile Thr Glu Phe Phe Ser Val Gly Ala
705                 710                 715                 720
Arg Gln Ala Glu Ala Ala Lys Asn Glu
                725

<210> SEQ ID NO 30
<211> LENGTH: 549
```

```
<212> TYPE: PRT
<213> ORGANISM: Beta vulgaris

<400> SEQUENCE: 30

Met Ser Glu Gly Thr Asn Lys Ala Met Ser Asp Pro Pro Thr Thr
1               5                   10                  15

Ala Ser Lys Val Ile Ala Asp Phe Asp Pro Leu Lys Lys Pro Pro Lys
            20                  25                  30

Arg Asn Lys Phe Ala Phe Ala Cys Ala Thr Leu Ala Ser Met Thr Ser
                35                  40                  45

Val Leu Leu Gly Tyr Asp Ile Gly Val Met Ser Gly Ala Ile Ile Tyr
    50                  55                  60

Leu Lys Glu Asp Trp His Ile Ser Asp Thr Gln Ile Gly Val Leu Val
65                  70                  75                  80

Gly Ile Leu Asn Ile Tyr Cys Leu Phe Gly Ser Phe Ala Ala Gly Arg
                85                  90                  95

Thr Ser Asp Trp Ile Gly Arg Arg Tyr Thr Ile Val Leu Ala Gly Ala
                100                 105                 110

Ile Phe Phe Val Gly Ala Leu Leu Met Gly Phe Ala Thr Asn Tyr Ala
            115                 120                 125

Phe Leu Met Val Gly Arg Phe Val Thr Gly Ile Gly Val Gly Tyr Ala
    130                 135                 140

Leu Met Ile Ala Pro Val Tyr Thr Ala Glu Val Ser Pro Ala Ser Ser
145                 150                 155                 160

Arg Gly Phe Leu Thr Ser Phe Pro Glu Val Phe Ile Asn Ala Gly Ile
                165                 170                 175

Leu Leu Gly Tyr Ile Ser Asn Leu Ala Phe Ser Ser Leu Pro Thr His
            180                 185                 190

Leu Ser Trp Arg Phe Met Leu Gly Ile Gly Ala Ile Pro Ser Ile Phe
    195                 200                 205

Leu Ala Ile Gly Val Leu Ala Met Pro Glu Ser Pro Arg Trp Leu Val
    210                 215                 220

Met Gln Gly Arg Leu Gly Asp Ala Lys Lys Val Leu Asn Arg Ile Ser
225                 230                 235                 240

Asp Ser Pro Glu Glu Ala Gln Leu Arg Leu Ser Glu Ile Lys Gln Thr
                245                 250                 255

Ala Gly Ile Pro Ala Glu Cys Asp Glu Asp Ile Tyr Lys Val Glu Lys
            260                 265                 270

Thr Lys Ile Lys Ser Gly Asn Ala Val Trp Lys Glu Leu Phe Phe Asn
    275                 280                 285

Pro Thr Pro Ala Val Arg Arg Ala Val Ile Ala Gly Ile Gly Ile His
    290                 295                 300

Phe Phe Gln Gln Ala Ser Gly Ile Asp Ala Val Val Leu Tyr Ser Pro
305                 310                 315                 320

Arg Ile Phe Gln Ser Ala Gly Ile Thr Asn Ala Arg Lys Gln Leu Leu
                325                 330                 335

Ala Thr Val Ala Val Gly Val Val Lys Thr Leu Phe Ile Leu Val Ala
            340                 345                 350

Thr Phe Gln Leu Asp Lys Tyr Gly Arg Arg Pro Leu Leu Leu Thr Ser
    355                 360                 365

Val Gly Gly Met Ile Ile Ala Ile Leu Thr Leu Ala Met Ser Leu Thr
    370                 375                 380

Val Ile Asp His Ser His His Lys Ile Thr Trp Ala Ile Ala Leu Cys
385                 390                 395                 400
```

-continued

```
Ile Thr Met Val Cys Ala Val Val Ala Ser Phe Ser Ile Gly Leu Gly
                405                 410                 415

Pro Ile Thr Trp Val Tyr Ser Ser Glu Val Phe Pro Leu Arg Leu Arg
                420                 425                 430

Ala Gln Gly Thr Ser Met Gly Val Ala Val Asn Arg Val Val Ser Gly
            435                 440                 445

Val Ile Ser Ile Phe Phe Leu Pro Leu Ser His Lys Ile Thr Thr Gly
        450                 455                 460

Gly Ala Phe Phe Leu Phe Gly Gly Ile Ala Ile Ile Ala Trp Phe Phe
465                 470                 475                 480

Phe Leu Thr Phe Leu Pro Glu Thr Arg Gly Arg Thr Leu Glu Asn Met
                485                 490                 495

His Glu Leu Phe Glu Asp Phe Arg Trp Arg Glu Ser Phe Pro Gly Asn
                500                 505                 510

Lys Ser Asn Asn Asp Glu Asn Ser Thr Arg Lys Gln Ser Asn Gly Asn
            515                 520                 525

Asp Lys Ser Gln Val Gln Leu Gly Glu Thr Thr Thr Ser Thr Thr Val
        530                 535                 540

Thr Asn Asp Asn His
545
```